(12) United States Patent
Fatheree et al.

(10) Patent No.: US 9,181,206 B2
(45) Date of Patent: *Nov. 10, 2015

(54) DUAL-ACTING OXAZOLE ANTIHYPERTENSIVE AGENTS

(71) Applicants: Paul R. Fatheree, San Francisco, CA (US); Ryan Hudson, San Jose, CA (US); Robert Murray McKinnell, Millbrae, CA (US)

(72) Inventors: Paul R. Fatheree, San Francisco, CA (US); Ryan Hudson, San Jose, CA (US); Robert Murray McKinnell, Millbrae, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/062,004

(22) Filed: Oct. 24, 2013

(65) Prior Publication Data

US 2014/0194426 A1      Jul. 10, 2014

Related U.S. Application Data

(60) Continuation of application No. 13/682,299, filed on Nov. 20, 2012, now Pat. No. 8,598,170, which is a division of application No. 12/835,999, filed on Jul. 14, 2010, now Pat. No. 8,372,984.

(60) Provisional application No. 61/227,473, filed on Jul. 22, 2009.

(51) Int. Cl.
| | |
|---|---|
| *C07D 413/14* | (2006.01) |
| *C07D 413/10* | (2006.01) |
| *C07D 263/34* | (2006.01) |
| *C07D 413/12* | (2006.01) |
| *C07D 263/38* | (2006.01) |
| *A61K 31/421* | (2006.01) |
| *A61K 31/422* | (2006.01) |
| *A61K 31/4245* | (2006.01) |
| *A61K 31/4439* | (2006.01) |
| *A61K 31/497* | (2006.01) |
| *A61K 31/506* | (2006.01) |
| *A61K 31/5377* | (2006.01) |

(52) U.S. Cl.
CPC ............ *C07D 263/34* (2013.01); *A61K 31/421* (2013.01); *A61K 31/422* (2013.01); *A61K 31/4245* (2013.01); *A61K 31/4439* (2013.01); *A61K 31/497* (2013.01); *A61K 31/506* (2013.01); *A61K 31/5377* (2013.01); *C07D 263/38* (2013.01); *C07D 413/10* (2013.01); *C07D 413/12* (2013.01); *C07D 413/14* (2013.01)

(58) Field of Classification Search
None
See application file for complete search history.

(56) References Cited

U.S. PATENT DOCUMENTS

| | | |
|---|---|---|
| 4,513,009 A | 4/1985 | Roques et al. |
| 4,610,816 A | 9/1986 | Berger |
| 4,722,810 A | 2/1988 | Delaney et al. |
| 4,929,641 A | 5/1990 | Haslanger et al. |
| 5,030,654 A | 7/1991 | Barnish et al. |
| 5,138,069 A | 8/1992 | Carini et al. |
| 5,155,100 A | 10/1992 | Erion et al. |
| 5,183,899 A | 2/1993 | Naka et al. |
| 5,192,781 A | 3/1993 | Bru-Magniez et al. |
| 5,217,996 A | 6/1993 | Ksander |
| 5,270,317 A | 12/1993 | Bernhart et al. |
| 5,294,632 A | 3/1994 | Erion et al. |
| 5,399,578 A | 3/1995 | Buhlmayer et al. |
| 5,444,081 A | 8/1995 | Gleason et al. |
| 5,508,272 A | 4/1996 | Robl |
| 5,587,375 A | 12/1996 | Robl |
| 5,591,762 A | 1/1997 | Hauel et al. |
| 5,616,599 A | 4/1997 | Yanagisawa et al. |
| 5,705,517 A | 1/1998 | Naka et al. |
| 5,864,043 A | 1/1999 | Narr et al. |

(Continued)

FOREIGN PATENT DOCUMENTS

| | | |
|---|---|---|
| EP | 0 361 365 A1 | 4/1990 |
| EP | 0 437 103 A2 | 7/1991 |

(Continued)

OTHER PUBLICATIONS

Ashton et al., "Nonpeptide Angiotensin II Antagonists Derived from 4H-1,2,4-triazoles and 3H-Imidazo[1,2-b][1,2,4]triazoles", J. Med. Chem., 36, 591-609 (1993).

(Continued)

*Primary Examiner* — Dennis Heyer
(74) *Attorney, Agent, or Firm* — Jeffrey A. Hagenah

(57) ABSTRACT

In one aspect, the invention relates to compounds having the formula:

(I)

wherein: Ar, Z, $R^3$, $R^4$ and $R^5$ are as defined in the specification, or a pharmaceutically acceptable salt thereof. These compounds have $AT_1$ receptor antagonist activity and neprilysin inhibition activity. In another aspect, the invention relates to pharmaceutical compositions comprising such compounds; methods of using such compounds; and process and intermediates for preparing such compounds.

16 Claims, No Drawings

(56) References Cited

U.S. PATENT DOCUMENTS

| | | | |
|---|---|---|---|
| 6,090,828 | A | 7/2000 | Reitz |
| 6,602,866 | B2 | 8/2003 | Flynn et al. |
| 6,777,443 | B2 | 8/2004 | Fink |
| 6,852,745 | B2 | 2/2005 | Murugesan et al. |
| 7,060,721 | B1 | 6/2006 | Oku et al. |
| 7,777,077 | B2 | 8/2010 | Choi et al. |
| 7,834,041 | B2 | 11/2010 | Choi et al. |
| 7,863,309 | B2 | 1/2011 | Choi et al. |
| 7,879,896 | B2 | 2/2011 | Allegretti et al. |
| 7,956,054 | B2 | 6/2011 | Fatheree et al. |
| 7,989,484 | B2 | 8/2011 | Allegretti et al. |
| 8,013,005 | B2 | 9/2011 | Allegretti et al. |
| 8,212,052 | B2 | 7/2012 | Choi et al. |
| 8,481,549 | B2 | 7/2013 | Fatheree et al. |
| 2003/0144215 | A1 | 7/2003 | Ksander et al. |
| 2004/0048911 | A1 | 3/2004 | Reitz et al. |
| 2006/0046978 | A1 | 3/2006 | Pierau et al. |
| 2008/0318951 | A1 | 12/2008 | Allegretti et al. |

FOREIGN PATENT DOCUMENTS

| | | | |
|---|---|---|---|
| EP | 0 505 954 | A1 | 9/1992 |
| EP | 0 726 072 | A2 | 8/1996 |
| EP | 0 997 147 | A1 | 5/2000 |
| JP | 06 184086 | | 7/1994 |
| JP | 07 048360 | | 2/1995 |
| JP | 2003 048874 | | 2/2003 |
| WO | WO 92/13564 | | 8/1992 |
| WO | WO 00/01389 | A2 | 1/2000 |
| WO | WO 2006/027680 | A1 | 3/2006 |
| WO | WO 2006/086456 | A2 | 8/2006 |
| WO | WO 2007/045663 | A2 | 4/2007 |
| WO | WO 2007/056546 | A1 | 5/2007 |
| WO | WO 2007/106708 | A2 | 9/2007 |
| WO | WO 2007/109456 | A2 | 9/2007 |
| WO | WO 2008/142576 | A2 | 11/2008 |

OTHER PUBLICATIONS

Bioisostere Definition, www.chemicool.com/definition/bioisostere.html. Mar. 23, 2012.

Fournie-Zaluski et al., "Design of Orally Active Dual Inhibitors of Neutral Endopeptidase and Angiotensin-Converting Enzyme with long Duration of Action" *Journal of Medicinal Chemistry* 39:2594-2608 (1996).

Gardiner et al., "Regional hemodynamic effects of neutral endopeptidase inhibition and angiotensin (AT1) receptor antagonism alone or in combination in conscious spontaneously hypertensive rats", The Journal of Pharmacology and Experimental Therapeutics, vol. 319 No. 1, pp. 340-348 (2006).

Kaspady et al., "Synthesis, Antibacterial Activity of 2,4-disubstituted Oxazoles and Thiazoles as Bioisosteres", Letters in Drug Design & Discovery, 6: 21-28 (2009).

Mallamo et al, "Antiandrogenic Steroidal Sulfonyl Heterocycles, Utility of Electrostatic Complementarity in Defining Bioisosteric Sulfonyl Heterocycles", Journal of Medicinal Chemistry, 35(10): 1663-1670 (1992).

Middlemiss et al., "Benzofuran based angiotensin II antagonists related to GR117289: Part II; amino acid amides", Bioorganic & Medicinal Chemistry Letters, vol. 3, No. 10, pp. 2043-2046 (1993).

Pu et al., "The effect of combined AT1 receptor antagonist and neutral endopeptidase (NEP) inhibitor compared to the dual angiotensin converting enzyme inhibitor/NEP on endothelial function and vascular remodeling of SHRSP", Abstract presented at the Canadian Cardiovascular Congress (Oct. 2004).

Robl et al., "Recent advances in the design and development of vasopeptidase inhibitors", Expert Opinion on Therapeutic Patents, 9(12), pp. 1665-1677 (1999).

Shah et al., "Angiotensin II—$AT_1$ Receptor Antagonist: design, synthesis and evaluation of substituted carboxamido benzoimidazole derivatives",*European Journal of Medicinal Chemistry*, 43(9), pp. 1808-1812 (2008).

International Search Report for PCT/US2010/041908 dated Oct. 14, 2010.

DUAL-ACTING OXAZOLE ANTIHYPERTENSIVE AGENTS

CROSS-REFERENCE TO RELATED APPLICATIONS

This application is a continuation of U.S. Ser. No. 13/682,299, now allowed; which is a divisional of U.S. Ser. No. 12/835,999, now U.S. Pat. No. 8,372,984; which claims the benefit of U.S. Provisional Application No. 61/227,473, filed on Jul. 22, 2009; the entire disclosures of which are incorporated herein by reference.

BACKGROUND OF THE INVENTION

1. Field of the Invention

The present invention relates to novel compounds having angiotensin II type 1 ($AT_1$) receptor antagonist activity and neprilysin-inhibition activity. The invention also relates to pharmaceutical compositions comprising such compounds, processes and intermediates for preparing such compounds and methods of using such compounds to treat diseases such as hypertension.

2. State of the Art

The aim of antihypertensive therapy is to lower blood pressure and prevent hypertension-related complications such as myocardial infarction, stroke, and renal disease. For patients with uncomplicated hypertension (that is, no risk factors, target organ damage, or cardiovascular disease), it is hoped that reducing blood pressure will prevent development of cardiovascular and renal comorbidities, conditions that exist at the same time as the primary condition in the same patient. For those patients with existing risk factors or comorbidities, the therapeutic target is the slowing of comorbid disease progression and reduced mortality.

Physicians generally prescribe pharmacological therapies for patients whose blood pressure cannot be adequately controlled by dietary and/or lifestyle modifications. Commonly used therapeutic classes act to promote diuresis, adrenergic inhibition, or vasodilation. A combination of drugs is often prescribed, depending upon what comorbidities are present.

There are five common drug classes used to treat hypertension: diuretics, which include thiazide and thiazide-like diuretics such as hydrochlorothiazide, loop diuretics such as furosemide, and potassium-sparing diuretics such as triamterene; $β_1$ adrenergic receptor blockers such as metoprolol succinate and carvedilol; calcium channel blockers such as amlodipine; angiotensin-converting enzyme (ACE) inhibitors such as captopril, benazepril, enalapril, enalaprilat, lisinopril, quinapril, and ramipril; and $AT_1$ receptor antagonists, also known as angiotensin II type 1 receptor blockers (ARBs), such as candesartan cilexetil, eprosartan, irbesartan, losartan, olmesartan medoxomil, telmisartan, and valsartan. Combinations of these drugs are also administered, for example, a calcium channel blocker (amlodipine) and an ACE inhibitor (benazepril), or a diuretic (hydrochlorothiazide) and an ACE inhibitor (enalapril). All of these drugs, when used appropriately, are effective in the treatment of hypertension. Nevertheless, both efficacy and tolerability should be further improved in new drugs targeting hypertension. Despite the availability of many treatment options, the recent National Health And Nutrition Examination Survey (NHANES) demonstrated that only about 50% of all treated patients with hypertension achieve adequate blood pressure control. Furthermore, poor patient compliance due to tolerability issues with available treatments further reduces treatment success.

In addition, each of the major classes of antihypertensive agents have some drawbacks. Diuretics can adversely affect lipid and glucose metabolism, and are associated with other side effects, including orthostatic hypotension, hypokalemia, and hyperuricemia. Beta blockers can cause fatigue, insomnia, and impotence; and some beta blockers can also cause reduced cardiac output and bradycardia, which may be undesirable in some patient groups. Calcium channel blockers are widely used but it is debatable as to how effectively these drugs reduce fatal and nonfatal cardiac events relative to other drug classes. ACE inhibitors can cause coughing, and rarer side effects include rash, angioedema, hyperkalemia, and functional renal failure. $AT_1$ receptor antagonists are equally effective as ACE inhibitors but without the high prevalence of cough.

Neprilysin (neutral endopeptidase, EC 3.4.24.11) (NEP), is an endothelial membrane bound $Zn^{2+}$ metallopeptidase found in many tissues, including the brain, kidney, lungs, gastrointestinal tract, heart, and peripheral vasculature. NEP is responsible for the degradation and inactivation of a number of vasoactive peptides, such as circulating bradykinin and angiotensin peptides, as well as the natriuretic peptides, the latter of which have several effects including vasodilation and diuresis. Thus, NEP plays an important role in blood pressure homeostasis. NEP inhibitors have been studied as potential therapeutics, and include thiorphan, candoxatril, and candoxatrilat. In addition, compounds have also been designed that inhibit both NEP and ACE, and include this class of compounds are described in Robl et al. (1999) *Exp. Opin. Ther. Patents* 9(12): 1665-1677.

There may be an opportunity to increase anti-hypertensive efficacy when combining $AT_1$ receptor antagonism and NEP inhibition, as evidenced by $AT_1$ receptor antagonist/NEP inhibitor combinations described in WO 9213564 to Darrow et al (Schering Corporation); US20030144215 to Ksander et al.; Pu et al., Abstract presented at the Canadian Cardiovascular Congress (October 2004); and Gardiner et al. (2006) *JPET* 319:340-348; and WO 2007/045663 (Novartis AG) to Glasspool et al.

Recently, WO 2007/056546 (Novartis AG) to Feng et al. has described complexes of an $AT_1$ receptor antagonist and a NEP inhibitor, where an $AT_1$ receptor antagonist compound is non-covalently bound to a NEP inhibitor compound, or where the antagonist compound is linked via non-covalent bonding to the inhibitor compound.

In spite of the advances in the art, there remains a need for a highly efficacious monotherapy with multiple mechanisms of action leading to levels of blood pressure control that can currently only be achieved with combination therapy. Thus, although various hypertensive agents are known, and administered in various combinations, it would be highly desirable to provide compounds having both $AT_1$ receptor antagonist activity and NEP inhibition activity in the same molecule. Compounds possessing both of these activities are expected to be particularly useful as therapeutic agents since they would exhibit antihypertensive activity through two independent modes of action while having single molecule pharmacokinetics.

In addition, such dual-acting compounds are also expected to have utility to treat a variety of other diseases that can be treated by antagonizing the $AT_1$ receptor and/or inhibiting the NEP enzyme.

SUMMARY OF THE INVENTION

The present invention provides novel compounds that have been found to possess $AT_1$ receptor antagonist activity and neprilysin (NEP) enzyme inhibition activity. Accordingly, compounds of the invention are expected to be useful and advantageous as therapeutic agents for treating conditions such as hypertension and heart failure.

One aspect of the invention relates to a compound of formula I:

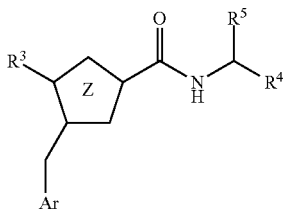

where: Z is an oxazole selected from:

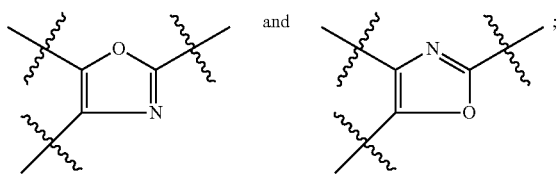 [SMILES: *c1nc(*)c(*)o1 ; *c1nc(*)c(*)o1]

Ar is selected from:

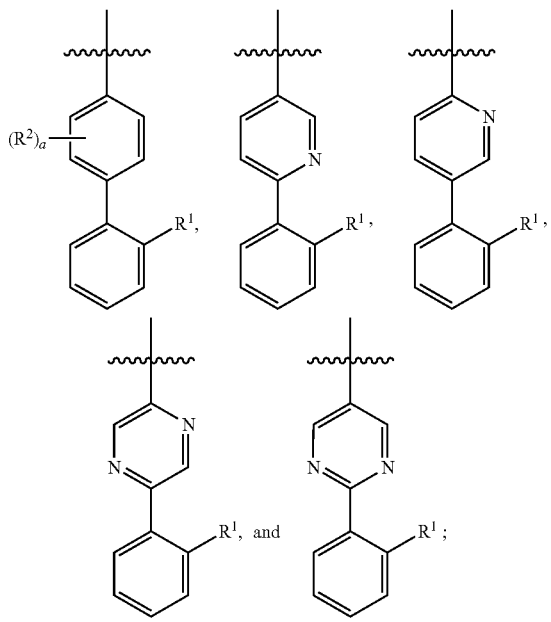

$R^1$ is selected from —COOR, —SO$_2$NHC(O)R$^{1a}$, tetrazolyl,

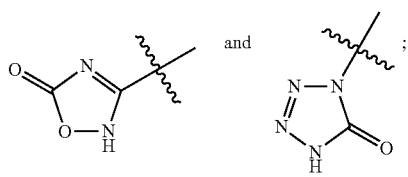

where $R^{1a}$ is —C$_{1-6}$alkyl, —C$_{0-6}$alkylene-OR, —C$_{3-7}$cycloalkyl, —C$_{0-5}$alkylene-NRR, pyridyl, isoxazolyl, methyl- isoxazolyl, pyrrolidinyl, morpholinyl, and phenyl optionally substituted with halo; where each R is independently selected from H and —C$_{1-6}$alkyl;

a is 0, 1, or 2; $R^2$ is F;

$R^3$ is selected from —C$_{2-5}$alkyl and —O—C$_{1-5}$alkyl;

$R^4$ is selected from —CH$_2$—SR$^{4a}$, —CH$_2$—N(OH)C(O) H, —CH(R$^{4b}$)C(O)NH(OH), and —CH(R$^{4b}$)COOR$^{4c}$; where R$^{4a}$ is H or —C(O)—C$_{1-6}$alkyl; R$^{4b}$ is H or —OH; and R$^{4a}$ is H or —C$_{1-6}$alkyl; and $R^5$ is selected from —C$_{1-6}$alkyl, —CH$_2$-furanyl, —CH$_2$-thiophenyl, benzyl, and benzyl substituted with one or more halo, —CH$_3$, or —CF$_3$ groups;

where each ring in Ar is optionally substituted with 1 to 3 substituents independently selected from —OH, —C$_{1-6}$alkyl, —C$_{2-4}$alkenyl, —C$_{2-4}$alkynyl, —CN, halo, —O—C$_{1-6}$alkyl, —S—C$_{1-6}$alkyl, —S(O)$_2$—C$_{1-4}$alkyl, -phenyl, —NO$_2$, —NH$_2$, —NH—C$_{1-6}$alkyl and —N(C$_{1-6}$alkyO$_2$, wherein each alkyl, alkenyl and alkynyl is optionally substituted with 1 to 5 fluoro atoms;

or a pharmaceutically acceptable salt thereof.

Another aspect of the invention relates to pharmaceutical compositions comprising a pharmaceutically acceptable carrier and a compound of the invention. Such compositions may optionally contain other therapeutic agents such as diuretics, β$_1$ adrenergic receptor blockers, calcium channel blockers, angiotensin-converting enzyme inhibitors, AT$_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, vasopressin receptor antagonists, and combinations thereof. Accordingly, in yet another aspect of the invention, a pharmaceutical composition comprises a compound of the invention, a second therapeutic agent, and a pharmaceutically acceptable carrier. Another aspect of the invention relates to a combination of active agents, comprising a compound of the invention and a second therapeutic agent. The compound of the invention can be formulated together or separately from the additional agent(s). When formulated separately, a pharmaceutically acceptable carrier may be included with the additional agent(s). Thus, yet another aspect of the invention relates to a combination of pharmaceutical compositions, the combination comprising: a first pharmaceutical composition comprising a compound of the invention and a first pharmaceutically acceptable carrier; and a second pharmaceutical composition comprising a second therapeutic agent and a second pharmaceutically acceptable carrier. In another aspect, the invention relates to a kit containing such pharmaceutical compositions, for example where the first and second pharmaceutical compositions are separate pharmaceutical compositions.

Compounds of the invention possess both AT$_1$ receptor antagonist activity and NEP enzyme inhibition activity, and are therefore expected to be useful as therapeutic agents for treating patients suffering from a disease or disorder that is treated by antagonizing the AT$_1$ receptor and/or inhibiting the NEP enzyme. Thus, one aspect of the invention relates to a method of treating patients suffering from a disease or disorder that is treated by antagonizing the AT$_1$ receptor and/or inhibiting the NEP enzyme, comprising administering to a patient a therapeutically effective amount of a compound of the invention. Another aspect of the invention relates to a method of treating hypertension or heart failure, comprising administering to a patient a therapeutically effective amount of a compound of the invention. Still another aspect of the invention relates to a method for antagonizing an AT$_1$ receptor in a mammal comprising administering to the mammal, an $AT_1$ receptor-antagonizing amount of a compound of the invention. Yet another aspect of the invention relates to a method for inhibiting a NEP enzyme in a mammal comprising administering to the mammal, a NEP enzyme-inhibiting amount of a compound of the invention.

Compounds of the invention that are of particular interest include those that exhibit an inhibitory constant ($pk_i$) for binding to an $AT_1$ receptor greater than or equal to about 5.0; in particular those having a $pK_i$ greater than or equal to about 6.0; in one embodiment those having a $pK_i$ greater than or equal to about 7.0; more particularly those having a $pK_i$ greater than or equal to about 8.0; and in yet another embodiment, those having a $pK_i$ within the range of about 8.0-10.0. Compounds of particular interest also include those having a NEP enzyme inhibitory concentration ($pIC_{50}$) greater than or equal to about 5.0; in one embodiment those having a $pIC_{50}$ greater than or equal to about 6.0; in particular those having a $pIC_{50}$ greater than or equal to about 7.0; and most particularly those having a $pIC_{50}$ within the range of about 7.0-10.0. Compounds of further interest include those having a $pK_i$ for binding to an $AT_1$ receptor greater than or equal to about 7.5 and having a NEP enzyme $pIC_{50}$ greater than or equal to about 7.0.

Since compounds of the invention possess $AT_1$ receptor antagonist activity and NEP inhibition activity, such compounds are also useful as research tools. Accordingly, one aspect of the invention relates to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include an $AT_1$ receptor binding assay and a NEP enzyme inhibition assay. Still another aspect of the invention relates to a method of studying a biological system or sample comprising an $AT_1$ receptor, a NEP enzyme, or both, the method comprising: (a) contacting the biological system or sample with a compound of the invention; and (b) determining the effects caused by the compound on the biological system or sample.

Yet another aspect of the invention relates to processes and intermediates useful for preparing compounds of the invention. Accordingly, another aspect of the invention relates to a process of preparing compounds of the invention comprising the step of coupling a compound of formula 1 with a compound of formula 2:

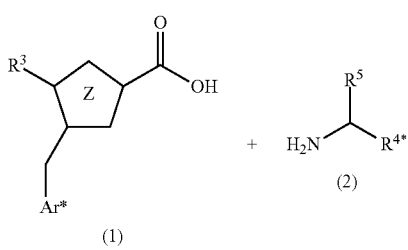

where: Ar* represents Ar—$R^{1*}$, where $R^{1*}$ is $R^1$ or a protected form of $R^1$; and $R^{4*}$ represents $R^4$ or a protected form of $R^4$; and optionally deprotecting the product when $R^{1*}$ is a protected form of $R^1$ and/or $R^{4*}$ is a protected form of $R^4$. Another aspect of the invention relates to a process of preparing a pharmaceutically acceptable salt of a compound of formula I, comprising contacting a compound of formula I in free acid or base form with a pharmaceutically acceptable base or acid. In other aspects, the invention relates to products prepared by any of the processes described herein, as well as novel intermediates used in such process. In one aspect of the invention novel intermediates have formula V, VI or VII, as defined herein.

Yet another aspect of the invention relates to the use of a compound of formula I or a pharmaceutically acceptable salt thereof, for the manufacture of a medicament, especially for the manufacture of a medicament useful for treating hypertension or heart failure. Another aspect of the invention relates to use of a compound of the invention for antagonizing an $AT_1$ receptor or for inhibiting a NEP enzyme in a mammal. Still another aspect of the invention relates to the use of a compound of the invention as a research tool. Other aspects and embodiments of the invention are disclosed herein.

DETAILED DESCRIPTION OF THE INVENTION

In one aspect, the invention relates to compounds of formula I:

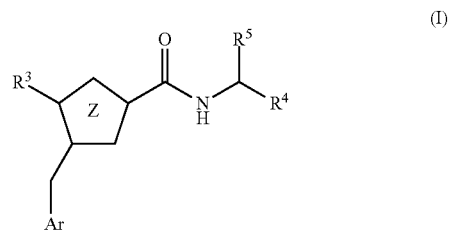

or a pharmaceutically acceptable salt thereof.

As used herein, the term "compound of the invention" includes all compounds encompassed by formula I such as the species embodied in formulas II, III, IV and V. In addition, the compounds of the invention may also contain several basic or acidic groups (for example, amino or carboxyl groups) and therefore, such compounds can exist as a free base, free acid, or in various salt forms. All such salt forms are included within the scope of the invention. Furthermore, the compounds of the invention may also exist as prodrugs. Accordingly, those skilled in the art will recognize that reference to a compound herein, for example, reference to a "compound of the invention" or a "compound of formula I" includes a compound of formula I as well as pharmaceutically acceptable salts and prodrugs of that compound unless otherwise indicated. Further, the term "or a pharmaceutically acceptable salt and/or prodrug thereof" is intended to include all permutations of salts and prodrugs, such as a pharmaceutically acceptable salt of a prodrug. Furthermore, solvates of compounds of formula I are included within the scope of this invention.

The compounds of formula I may contain one or more chiral centers and therefore, these compounds may be prepared and used in various stereoisomeric forms. Accordingly, the invention relates to racemic mixtures, pure stereoisomers (enantiomers or diastereomers), stereoisomer-enriched mixtures, and the like unless otherwise indicated. When a chemical structure is depicted herein without any stereochemistry, it is understood that all possible stereoisomers are encompassed by such structure. Thus, for example, the term "compound of formula I" is intended to include all possible stereoisomers of the compound. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual enantiomers may be obtained by numerous methods that are well known in the art, including chiral chromatography using a suitable chiral stationary phase or support, or by chemically converting them into diastereomers, separating the diastereomers by conventional means such as chromatography or recrystallization, then regenerating the original enantiomers. Additionally, where applicable, all cis-trans or E/Z isomers (geometric isomers), tautomeric forms and topoisomeric forms of the compounds of the invention are included within the scope of the invention unless otherwise specified.

One possible chiral center could be present at the carbon on the —CHR$^4$R$^5$ group, when R$^5$ is a group such as —C$_{1-6}$alkyl, for example —CH$_2$CH(CH$_3$)$_2$. This chiral center is present at the carbon atom indicated by the symbol *:

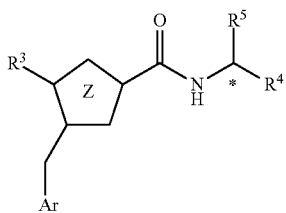

In one embodiment of the invention, the carbon atom identified by the symbol * has the (R) configuration. In this embodiment, compounds of formula I have the (R) configuration at the carbon atom identified by the symbol * or are enriched in a stereoisomeric form having the (R) configuration at this carbon atom. In another embodiment, the carbon atom identified by the symbol * has the (S) configuration. In this embodiment, compounds of formula I have the (S) configuration at the carbon atom identified by the symbol * or are enriched in a stereoisomeric form having the (S) configuration at this carbon atom.

The compounds of the invention can also have two chiral centers on the —CHR$^4$R$^5$ group, for example when R$^4$ is —CH(OH)COOH and R$^5$ is benzyl. These chiral centers are present at the carbons atom indicated by the symbols * and **:

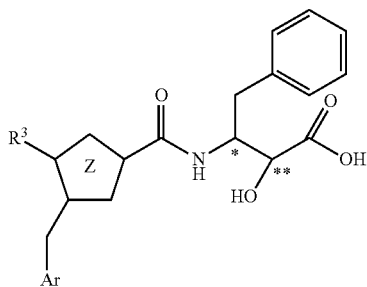

In such cases, four possible diastereomers can exist. For example, both carbon atoms can have the (R) configuration, and in such an embodiment, compounds of formula I have the (R) configuration at the carbon atoms identified by the symbols * and ** or are enriched in a stereoisomeric form having the (R,R) configuration at these atoms. In another embodiment, both carbon atoms can have the (S) configuration, and in such an embodiment, compounds of formula I have the (S,S) configuration at the carbon atoms identified by the symbols * and ** or are enriched in a stereoisomeric form having the (S) configuration at these atoms. In yet another embodiment, the carbon atom identified by the symbol * can have the (S) configuration and the carbon atom identified by the symbol ** can have the (R) configuration, and in such an embodiment, compounds of formula I have the (S,R) configuration at the carbon atoms identified by the symbols * and ** or are enriched in a stereoisomeric form having the (S,R) configuration at these atoms. In still another embodiment, the carbon atom identified by the symbol * can have the (R) configuration and the carbon atom identified by the symbol ** can have the (S) configuration, and in such an embodiment, compounds of formula I have the (R,S) configuration at the carbon atoms identified by the symbols * and ** or are enriched in a stereoisomeric form having the (R,S) configuration at these atoms.

In some cases, in order to optimize the therapeutic activity of the compounds of the invention, for example, as hypertensive agents, it may be desirable that the carbon atom identified by the symbols * and/or ** have a particular (R), (S), (R,R), (S,S), (S,R), or (R,S) configuration.

The compounds of the invention, as well as those compounds used in their synthesis, may also include isotopically-labeled compounds, that is, where one or more atoms have been enriched with atoms having an atomic mass different from the atomic mass predominately found in nature. Examples of isotopes that may be incorporated into the compounds of formula I, for example, include, but are not limited to, $^2$H, $^3$H, $^{13}$C, $^{14}$C, $^{15}$N, $^{18}$O, $^{17}$O, $^{35}$S, $^{36}$Cl, and $^{18}$F.

The compounds of formula I have been found to possess AT$_1$ receptor antagonizing activity and NEP enzyme inhibition activity. Among other properties, such compounds are expected to be useful as therapeutic agents for treating diseases such as hypertension. By combining dual activity into a single compound, double therapy can be achieved, that is, AT$_1$ receptor antagonist activity and NEP enzyme inhibition activity can be obtained using a single active component. Since pharmaceutical compositions containing one active component are typically easier to formulate than compositions containing two active components, such single-component compositions provide a significant advantage over compositions containing two active components. In addition, certain compounds of the invention have also been found to be selective for inhibition of the AT$_1$ receptor over the angiotensin II type 2 (AT$_2$) receptor, a property that may have therapeutic advantages.

The nomenclature used herein to name the compounds of the invention is illustrated in the Examples herein. This nomenclature has been derived using the commercially available AutoNom software (MDL, San Leandro, Calif.).

Representative Embodiments

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

In one aspect, the invention relates to compounds of formula I:

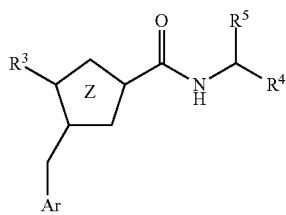

(I)

Z represents an oxazole selected from:

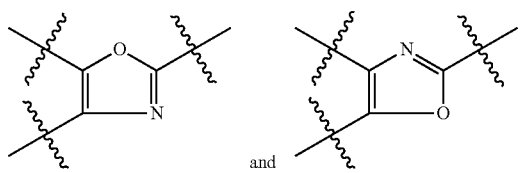

and

Thus, the compounds of the invention can also be depicted as formulas II and III:

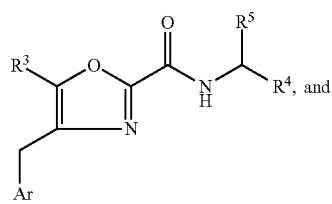

(II)

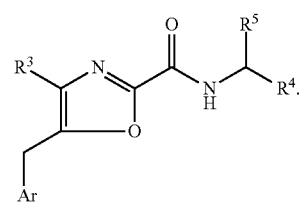

(III)

Ar represents an aryl group selected from:

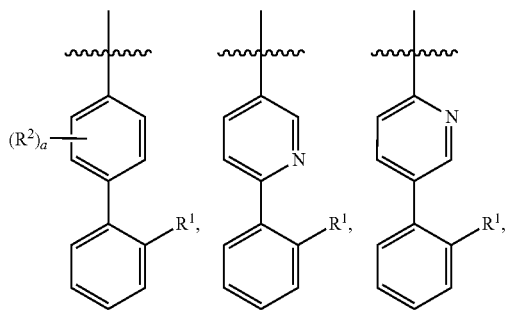

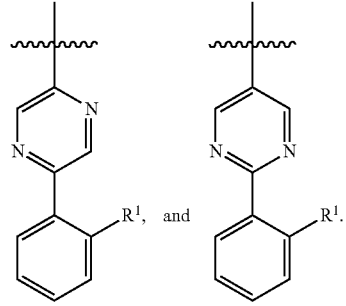

The integer "a" is 0, 1, or 2, and the $R^2$ group is fluoro. Exemplary fluoro-substituted Ar moieties include:

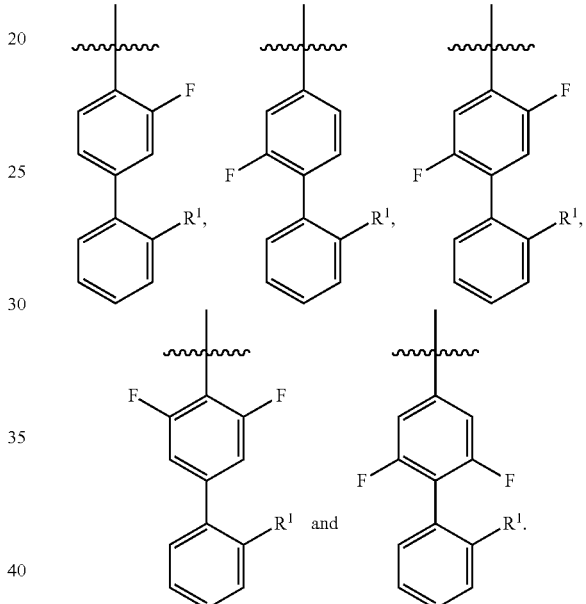

Each ring in Ar may also be substituted with 1 to 3 substituents independently selected from —OH, —$C_{1-6}$alkyl, —$C_{2-4}$alkenyl, —$C_{2-4}$alkynyl, —CN, halo, —O—$C_{1-6}$alkyl, —S—$C_{1-6}$alkyl, —S(O)—$C_{1-6}$alkyl, —S(O)$_2$—$C_{1-4}$alkyl, -phenyl, —$NO_2$, —$NH_2$, —NH—$C_{1-6}$alkyl and —N($C_{1-6}$alkyl)$_2$, wherein each alkyl, alkenyl and alkynyl is optionally substituted with 1 to 5 fluoro atoms.

$R^1$ is selected from —COOR, —$SO_2$NHC(O)$R^{1a}$, tetrazolyl,

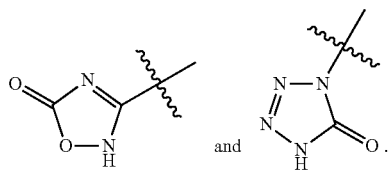 [SMILES: *c1nc(=O)o[nH]1 ; *n1nn[nH]c1=O]

The $R^{1a}$ moiety is —$C_{1-6}$alkyl, —$C_{0-6}$alkylene-OR, —$C_{3-7}$cycloalkyl, —$C_{0-5}$alkylene-NRR, pyridyl, isoxazolyl, methylisoxazolyl, pyrrolidinyl, morpholinyl, and phenyl optionally substituted with halo. Each R is independently selected from H and —$C_{1-6}$alkyl.

In one embodiment, $R^1$ is —COOR, for example, $R^1$ is —COOH or —COOCH$_3$.

In one particular embodiment, $R^1$ is —SO$_2$NHC(O)R$^{1a}$, where R$^{1a}$ is —C$_{1-6}$alkyl. Examples of this embodiment include —SO$_2$NHC(O)CH$_3$ and SO$_2$NHC(O)CH$_2$CH$_3$. In one particular embodiment, $R^1$ is tetrazolyl such as 1H-tetrazol-5-yl or 5H-tetrazol-5-yl.

In one particular embodiment, $R^1$ is —SO$_2$NHC(O)R$^{1a}$, where R$^{1a}$ is —C$_{0-6}$alkylene-OR. Examples of this embodiment include —SO$_2$NHC(O)OCH$_3$, —SO$_2$NHC(O)OCH$_2$CH$_3$, —SO$_2$NHC(O)CH$_2$OCH$_3$, —SO$_2$NHC(O)CH$_2$OH, —SO$_2$NHC(O)CH(CH$_3$)OH, —SO$_2$NHC(O)C(CH$_3$)$_2$OH, —SO$_2$NHC(O)CH$_2$OCH$_3$, and —SO$_2$NHC(O)(CH$_2$)$_2$OCH$_3$.

In another particular embodiment, $R^1$ is —SO$_2$NHC(O)R$^{1a}$, where R$^{1a}$ is —C$_{3-7}$cycloalkyl. Examples of this embodiment include —SO$_2$NHC(O)-cyclopropyl. In another particular embodiment, $R^1$ is —SO$_2$NHC(O)R$^{1a}$, where R$^{1a}$ is —C$_{0-5}$alkylene-NRR. Examples of this embodiment include SO$_2$NHC(O)NH(CH$_3$), —SO$_2$NHC(O)N(CH$_3$)$_2$, —SO$_2$NHC(O)NH(CH$_2$CH$_3$), and —SO$_2$NHC(O)C(CH$_3$)$_2$NH$_2$.

In another particular embodiment, $R^1$ is —SO$_2$NHC(O)R$^{1a}$, where R$^{1a}$ is pyridyl, for example, —SO$_2$NHC(O)-2-pyridyl, —SO$_2$NHC(O)-3-pyridyl, or —SO$_2$NHC(O)-4-pyridyl. The term "pyridyl" means a heterocyclic compound of the formula:

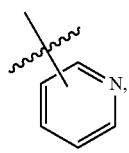

which is bonded to any available point of attachment and includes:

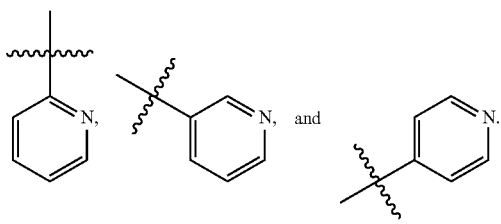 [SMILES: *c1ccccn1 ; *c1cccnc1 ; *c1ccncc1]

In another particular embodiment, $R^1$ is —SO$_2$NHC(O)R$^{1a}$, where R$^{1a}$ is isoxazolyl, for example, —SO$_2$NHC(O)-3-isoxazolyl, —SO$_2$NHC(O)-4-isoxazolyl, and —SO$_2$NHC(O)-5-isoxazolyl. The term "isoxazolyl" means a heterocyclic compound of the formula:

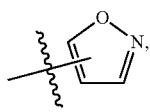

which is bonded to any available point of attachment and includes:

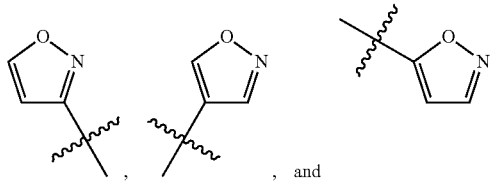

In one particular embodiment, $R^1$ is —SO$_2$NHC(O)R$^{1a}$, where R$^{1a}$ is methylisoxazolyl, for example —SO$_2$NHC(O)-3-isoxazolyl-5-methyl or —SO$_2$NHC(O)-5-isoxazolyl-3-methyl. The term "methylisoxazolyl" means a heterocyclic compound of the formula:

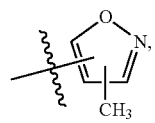

which is bonded to any available point of attachment and includes:

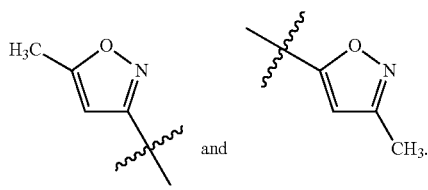

In another particular embodiment, $R^1$ is —SO$_2$NHC(O)R$^{1a}$, where R$^{1a}$ is pyrrolidinyl, for example, —SO$_2$NHC(O)-1-pyrrolidyl, —SO$_2$NHC(O)-2-pyrrolidyl, and —SO$_2$NHC(O)-3-pyrrolidyl. The term "pyrrolidinyl" means a heterocyclic compound of the formula:

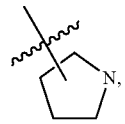

which is bonded to any available point of attachment and includes:

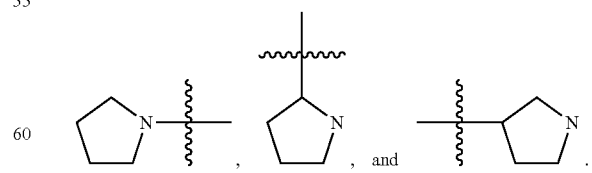

In one particular embodiment, $R^1$ is —SO$_2$NHC(O)R$^{1a}$, where R$^{1a}$ is morpholinyl, for example, —SO$_2$NHC(O)-4-morpholinyl. The term "morpholinyl" means a heterocyclic compound of the formula:

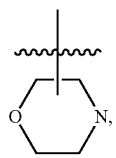

which is bonded to any available point of attachment and includes:

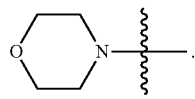 [SMILES: *N1CCOCC1]

In yet another particular embodiment, $R^1$ is —SO$_2$NHC(O)$R^{1a}$, where $R^{1a}$ is phenyl optionally substituted with halo. In one embodiment, the phenyl group is unsubstituted and $R^1$ is —SO$_2$NHC(O)phenyl. In another embodiment, the phenyl group is substituted with 1 or 2 halo atoms. In yet another embodiment, the halo atoms are fluoro atoms. Examples of this embodiment include —SO$_2$NHC(O)-2-fluorophenyl.

In still another particular embodiment, $R^1$ is tetrazol-5-yl. In yet another embodiment, $R^1$ is:

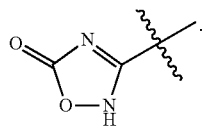 [SMILES: *c1nc(=O)o[nH]1]

And in yet another embodiment, $R^1$ is:

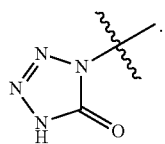

$R^3$ is selected from —C$_{2-5}$alkyl and —O—C$_{1-5}$alkyl. Examples of —C$_{2-5}$alkyl include —CH$_2$CH$_3$, —(CH$_2$)$_2$CH$_3$, —CH(CH$_3$)$_2$, —(CH$_2$)$_3$CH$_3$, —CH$_2$CH(CH$_3$)$_2$, —C(CH$_3$)$_3$, CH(CH$_3$)—CH$_2$CH$_3$, and —(CH$_2$)$_4$CH$_3$. In one embodiment, $R^3$ is propyl, ethyl, or butyl. Examples of —O—C$_{1-5}$alkyl include —OCH$_3$, —OCH$_2$CH$_3$, —O(CH$_2$)$_2$CH$_3$, and —OCH(CH$_3$)$_2$. In one embodiment, $R^3$ is ethoxy.

$R^4$ is selected from —CH$_2$—SR$^{4a}$, —CH$_2$—N(OH)C(O)H, —CH(R$^{4b}$)C(O)NH(OH), and —CH(R$^{4b}$)COOR$^{4c}$. The $R^{4a}$ moiety is H or —C(O)—C$_{1-6}$alkyl. The $R^{4b}$ moiety is H or —OH, and the $R^{4c}$ moiety is H or —C$_{1-6}$alkyl.

In one particular embodiment, $R^4$ is —CH$_2$—SR$^{4a}$. Examples of this embodiment include —CH$_2$SH and —CH$_2$—S—C(O)CH$_3$.

In another embodiment, $R^4$ is —CH$_2$N(OH)C(O)H. In one particular embodiment, $R^4$ is —CH(R$^{4b}$)C(O)NH(OH), such as —CH$_2$C(O)NH(OH) or —CH(OH)C(O)NH(OH).

In one embodiment, $R^4$ is —CH(R$^{4b}$)COOR$^{4c}$, where $R^{4b}$ H, examples of which include —CH$_2$COOH and —CH$_2$COOCH$_3$. In another embodiment, $R^4$ is —CH(R$^{4b}$)COOR$^{4c}$, where $R^{4b}$ is —OH, examples of which include —CH(OH)COOH and —CH(OH)COOCH$_3$.

In one embodiment, $R^4$ is —CH(R$^{4b}$)COOR$^{4c}$, where $R^{4b}$ H, and $R^5$ is benzyl substituted with one or more halo, —CH$_3$, or —CF$_3$ groups.

In one aspect, the invention relates to compounds of formula IV:

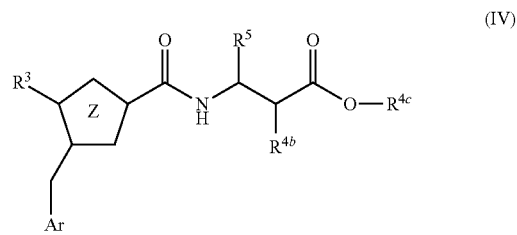

where Ar, $R^3$, $R^{4b}$, $R^{4c}$, and $R^5$ are as defined for formula I; or a pharmaceutically acceptable salt thereof.

In one embodiment, $R^4$ is selected from —CH$_2$—SR$^{4a}$, —CH$_2$—N(OH)C(O)H, —CH(R$^{4b}$)C(O)NH(OH), and —CH(R$^{4b}$)COOR$^{4c}$; where $R^{4a}$ and $R^{4c}$ are H; and $R^{4b}$ is as defined for formula I. In another aspect, these embodiments have formula II or III.

In yet another embodiment, $R^4$ is selected from —CH$_2$—SR and —CH(R$^{4b}$)COOR$^{4c}$; where $R^{4a}$ is —C(O)—C$_{1-6}$alkyl; $R^{4c}$ is —C$_{1-6}$alkyl; and $R^{4b}$ is as defined for formula I. In one aspect of the invention, these compounds may find particular utility as prodrugs or as intermediates in the synthetic procedures described herein. In another aspect, these embodiments have formula II or III.

$R^5$ is selected from —C$_{1-6}$alkyl, —CH$_2$-furanyl, —CH$_2$-thiophenyl, benzyl, and benzyl substituted with one or more halo, —CH$_3$, or —CF$_3$ groups. In one particular embodiment, $R^5$ is —C$_{1-6}$alkyl. Examples of this embodiment include i-butyl. In another embodiment, $R^5$ is —CH$_2$-furanyl such as —CH$_2$-furan-2-yl or —CH$_2$-furan-3-yl. In one particular embodiment, $R^5$ is —CH$_2$-thiophenyl such as —CH$_2$-thiophen-2-yl or —CH$_2$-thiophen-3-yl. In yet another particular embodiment, $R^5$ is benzyl. In still another embodiment, $R^5$ is benzyl substituted with one or more halo, —CH$_3$, or —CF$_3$ groups. Examples of this embodiment include 2-bromobenzyl, 2-chlorobenzyl, 2-fluorobenzyl, 3-fluorobenzyl, 4-fluorobenzyl, 2-methylbenzyl, and 2-trifluoromethylbenzyl.

In one particular embodiment, Ar is:

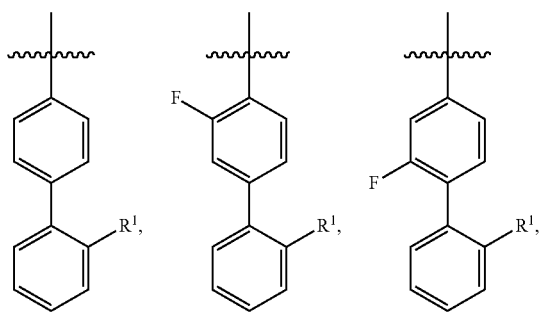

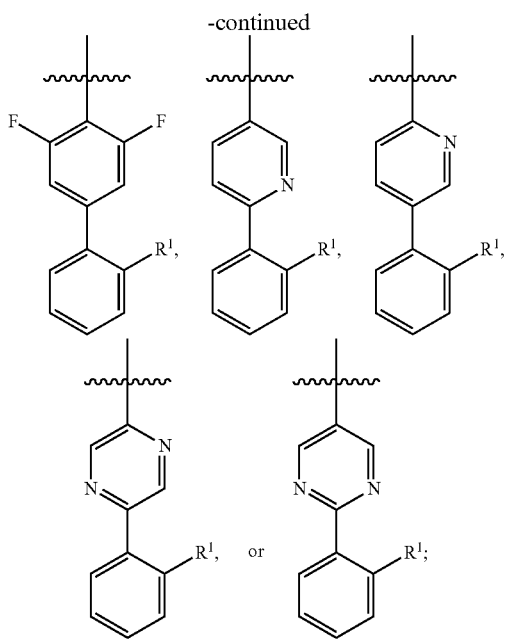

R¹ is —SO₂NHC(O)CH₃, —SO₂NHC(O)CH₂CH₃, —SO₂NHC(O)OCH₃, —SO₂NHC(O)OCH₂CH₃, —SO₂NHC(O)CH₂OCH₃, —SO₂NHC(O)CH₂OH, —SO₂NHC(O)CH(CH₃)OH, —SO₂NHC(O)C(CH₃)₂OH, —SO₂NHC(O)CH₂OCH₃, —SO₂NHC(O)(CH₂)₂OCH₃, —SO₂NHC(O)-cyclopropyl, —SO₂NHC(O)NH(CH₃), —SO₂NHC(O)N(CH₃)₂, —SO₂NHC(O)NH(CH₂CH₃), —SO₂NHC(O)C(CH₃)₂NH₂, —SO₂NHC(O)-2-pyridyl, —SO₂NHC(O)-4-pyridyl, —SO₂NHC(O)-5-isoxazolyl, —SO₂NHC(O)-3-isoxazolyl-5-methyl, —SO₂NHC(O)-1-pyrrolidyl, —SO₂NHC(O)-4-morpholinyl, —SO₂NHC(O)phenyl, —SO₂NHC(O)-2-fluorophenyl, 1H-tetrazol-5-yl,

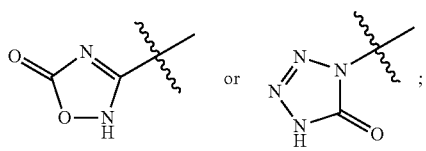 [SMILES: *c1nc(=O)o[nH]1 ; *n1nn[nH]c1=O]

R³ is propyl, ethyl, butyl, or ethoxy; R⁴ is —CH₂SH, —CH₂—S—C(O)CH₃, —CH₂N(OH)C(O)H, —CH₂C(O)NH(OH), —CH(OH)C(O)NH(OH), —CH(OH)COOH, CH(OH)COOCH₃, —CH₂COOH, or —CH₂COOCH₃; R⁵ is i-butyl, —CH₂-furan-2-yl, —CH₂-thiophen-3-yl, benzyl, 2-bromobenzyl, 2-chlorobenzyl, 2-fluorobenzyl, 3-fluorobenzyl, 4-fluorobenzyl, 2-methylbenzyl, or 2-trifluoromethylbenzyl; or a pharmaceutically acceptable salt thereof. In another aspect, this embodiment has formula II or III. In another aspect, when R⁴ is —CH(OH)COOH, CH(OH)COOCH₃, —CH₂COOH, or —CH₂COOCH₃, this embodiment has formula IV.

In addition, particular compounds of formula I that are of interest include those set forth in the Examples below, as well a pharmaceutically acceptable salt thereof.

DEFINITIONS

When describing the compounds, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "alkyl" means a monovalent saturated hydrocarbon group which may be linear or branched. Unless otherwise defined, such alkyl groups typically contain from 1 to 10 carbon atoms and include, for example, —C₁₋₄alkyl, —C₁₋₅alkyl, —C₂₋₅alkyl, —C₁₋₆alkyl, and —C₁₋₁₀alkyl. Representative alkyl groups include, by way of example, methyl, ethyl, n-propyl, isopropyl, n-butyl, s-butyl, isobutyl, t-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term as subscript. For example, the term "—C₁₋₆alkyl" means an alkyl group having from 1 to 6 carbon atoms, and the term "—C₃₋₇cycloalkyl" means a cycloalkyl group having from 3 to 7 carbon atoms, respectively, where the carbon atoms are in any acceptable configuration.

The term "alkylene" means a divalent saturated hydrocarbon group that may be linear or branched. Unless otherwise defined, such alkylene groups typically contain from 0 to 10 carbon atoms and include, for example, —C₀₋₁alkylene-, —C₀₋₂alkylene-, —C₀₋₃alkylene-, —C₀₋₅alkylene-, —C₀₋₆alkylene-, —C₁₋₂alkylene- and —C₁₋₁₂alkylene-. Representative alkylene groups include, by way of example, methylene, ethane-1,2-diyl ("ethylene"), propane-1,2-diyl, propane-1,3-diyl, butane-1,4-diyl, pentane-1,5-diyl and the like. It is understood that when the alkylene term include zero carbons such as —C₀₋₅alkylene- or —C₀₋₆alkylene-, such terms are intended to include the absence of carbon atoms, that is, the alkylene group is not present except for a covalent bond attaching the groups separated by the alkylene term.

The term "alkoxy" means a monovalent group of the formula —O-alkyl, where alkyl is as defined herein. Unless otherwise defined, such alkoxy groups typically contain from 1 to 10 carbon atoms and include, for example, —O—C₁₋₄alkyl and —O—C₁₋₅alkyl. Representative alkoxy groups include, by way of example, methoxy, ethoxy, n-propoxy, isopropoxy, n-butoxy, sec-butoxy, isobutoxy, t-butoxy and the like.

The term "cycloalkyl" means a monovalent saturated carbocyclic hydrocarbon group. Unless otherwise defined, such cycloalkyl groups typically contain from 3 to 10 carbon atoms and include, for example, —C₃₋₅cycloalkyl, —C₃₋₆cycloalkyl and —C₃₋₇cycloalkyl. Representative cycloalkyl groups include, by way of example, cyclopropyl, cyclobutyl, cyclopentyl, cyclohexyl and the like. The term "cycloalkylene" means a divalent aryl group such as —C₄₋₈cycloalkylene.

The term "halo" means fluoro, chloro, bromo and iodo.

As used herein, the phrase "having the formula" or "having the structure" is not intended to be limiting and is used in the same way that the term "comprising" is commonly used.

The term "optionally substituted" means that group in question may be unsubstituted or it may be substituted one or several times, such as 1 to 3 times or 1 to 5 times. For example, a phenyl group that is "optionally substituted" with halo atoms, may be unsubstituted, or it may contain 1, 2, 3, 4, or 5 halo atoms.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "protected derivatives thereof" means a derivative of the specified compound in which one or more functional groups of the compound are protected or blocked from undergoing undesired reactions with a protecting or blocking group. Functional groups that may be protected include, by way of example, carboxy groups, amino groups, hydroxyl groups, thiol groups, carbonyl groups and the like. Representative protecting groups for carboxy groups include esters (such as a p-methoxybenzyl ester), amides and hydrazides; for amino groups, carbamates (such as t-butoxycarbonyl) and amides; for hydroxyl groups, ethers and esters; for thiol groups, thioethers and thioesters; for carbonyl groups, acetals and ketals; and the like. Such protecting groups are well known to those skilled in the art and are described, for example, in T. W. Greene and G. M. Wuts, *Protecting Groups in Organic Synthesis*, Third Edition, Wiley, New York, 1999, and references cited therein.

As used herein, the term "prodrug" is intended to mean an inactive (or significantly less active) precursor of a drug that is converted into its active form in the body under physiological conditions, for example, by normal metabolic processes. The term is also intended to include certain protected derivatives of compounds of formula I that may be made prior to a final deprotection stage. Such compounds may not possess pharmacological activity at $AT_1$ and/or NEP, but may be administered orally or parenterally and thereafter metabolized in the body to form compounds of the invention which are pharmacologically active at $AT_1$ and/or NEP. Thus, all protected derivatives and prodrugs of compounds formula I are included within the scope of the invention. Prodrugs of compounds of formula I having a free carboxyl, sulfhydryl or hydroxy group can be readily synthesized by techniques that are well known in the art. These prodrug derivatives are then converted by solvolysis or under physiological conditions to be the free carboxyl, sulfhydryl and/or hydroxy compounds. Exemplary prodrugs include: esters including $C_{1-6}$alkylesters and aryl-$C_{1-6}$alkylesters, carbonate esters, hemi-esters, phosphate esters, nitro esters, sulfate esters, sulfoxides, amides, carbamates, azo-compounds, phosphamides, glycosides, ethers, acetals, ketals, and disulfides. In one embodiment, the compounds of formula I have a free sulfhydryl or a free carboxyl and the prodrug is an ester derivative thereof, i.e., the prodrug is a thioester such as —$SC(O)CH_3$ or an ester such as —$C(O)OCH_3$.

The term "solvate" means a complex or aggregate formed by one or more molecules of a solute, for example, a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

The term "therapeutically effective amount" means an amount sufficient to effect treatment when administered to a patient in need thereof, that is, the amount of drug needed to obtain the desired therapeutic effect. For example, a therapeutically effective amount for treating hypertension is an amount of compound needed to, for example, reduce, suppress, eliminate or prevent the symptoms of hypertension, or to treat the underlying cause of hypertension. In one embodiment, a therapeutically effective amount is that amount of drug needed to reduce blood pressure or the amount of drug needed to maintain normal blood pressure. On the other hand, the term "effective amount" means an amount sufficient to obtain a desired result, which may not necessary be a therapeutic result. For example, when studying a system comprising an $AT_1$ receptor, an "effective amount" may be the amount needed to antagonize the receptor.

The term "treating" or "treatment" as used herein means the treating or treatment of a disease or medical condition (such as hypertension) in a patient, such as a mammal (particularly a human) that includes one or more of the following: (a) preventing the disease or medical condition from occurring, that is, by prophylactic treatment of a patient; (b) ameliorating the disease or medical condition such as by eliminating or causing regression of the disease or medical condition in a patient; (c) suppressing the disease or medical condition such as by slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition, as well as test subjects in which compounds of the invention are being evaluated or being used in a assay, for example an animal model.

All other terms used herein are intended to have their ordinary meaning as understood by those of ordinary skill in the art to which they pertain.

General Synthetic Procedures

Compounds of the invention can be prepared from readily available starting materials using the following general methods, the procedures set forth in the Examples, or by using other methods, reagents, and starting materials that are known to those of ordinary skill in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (for example, reaction temperatures, times, mole ratios of reactants, solvents, pressures, etc.) are given, other process conditions can also be used unless otherwise stated. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Third Edition, Wiley, New York, 1999, and references cited therein. More specifically, the following abbreviations and reagents are used in the schemes presented below:

$P^1$ represents an "amino-protecting group," a term used herein to mean a protecting group suitable for preventing undesired reactions at an amino group. Representative amino-protecting groups include, but are not limited to, t-butoxycarbonyl (BOC), trityl (Tr), benzyloxycarbonyl (Cbz), 9-fluorenylmethoxycarbonyl (Fmoc), formyl, trimethylsilyl (TMS), t-butyldimethylsilyl (TBDMS), and the like. Standard deprotection techniques are used to remove the $P^1$ group. For example, a BOC group can be removed using an acidic reagent such as TFA in DCM or HCl in 1,4-dioxane, while a Cbz group can be removed by employing catalytic hydrogenation conditions such as $H_2$ (1 atm) and 10% Pd/C in an alcoholic solvent ("$H_2$/Pd/C").

$P^2$ represents a "carboxy-protecting group," a term used herein to mean a protecting group suitable for preventing undesired reactions at a carboxy group. Representative carboxy-protecting groups include, but are not limited to, methyl, ethyl, t-butyl, benzyl (Bn), p-methoxybenzyl (PMB), 9-fluorenylmethyl (Fm), trimethylsilyl (TMS), t-butyldimethylsilyl (TBDMS), diphenylmethyl (benzhydryl, DPM) and the like. Standard deprotection techniques and reagents are used to remove the $P^2$ group, and may vary depending upon which group is used. For example, sodium or lithium hydroxide is commonly used when $P^2$ is methyl, an acid such as TFA or HCl is commonly used when $P^2$ is t-butyl, and $H_2$/Pd/C may be used when $P^2$ is benzyl.

$P^3$ represents a "thiol-protecting group," a term used herein to mean a protecting group suitable for preventing undesired reactions at a thiol group. Representative thiol-protecting groups include, but are not limited to, ethers, esters such as —C(O)CH$_3$, and the like. Standard deprotection techniques and reagents such as NaOH, primary alkylamines, and hydrazine, may be used to remove the $P^3$ group.

$P^4$ represents a "tetrazole-protecting group," a term used herein to mean a protecting group suitable for preventing undesired reactions at a tetrazole group. Representative tetrazole-protecting groups include, but are not limited to trityl and diphenylmethyl. Standard deprotection techniques and reagents such as TFA in DCM or HCl in 1,4-dioxane may be used to remove the $P^4$ group.

$P^5$ represents a "hydroxyl-protecting group," a term that is used herein to mean a protecting group suitable for preventing undesired reactions at a hydroxyl group. Representative hydroxyl-protecting groups include, but are not limited to $C_{1-6}$alkyls, silyl groups including tri$C_{1-6}$alkylsilyl groups, such as trimethylsilyl (TMS), triethylsilyl (TES), and tert-butyldimethylsilyl (TBDMS); esters (acyl groups) including $C_{1-6}$alkanoyl groups, such as formyl, acetyl, and pivaloyl, and aromatic acyl groups such as benzoyl; arylmethyl groups such as benzyl (Bn), p-methoxybenzyl (PMB), 9-fluorenylmethyl (Fm), and diphenylmethyl (benzhydryl, DPM); and the like. Standard deprotection techniques and reagents are used to remove the $P^5$ group, and may vary depending upon which group is used. For example, $H_2$/Pd/C is commonly used when $P^5$ is benzyl, while NaOH is commonly used when $P^5$ is an acyl group.

$P^6$ represents a "sulfonamide-protecting group," a term that is used herein to mean a protecting group suitable for preventing undesired reactions at a sulfonamide group. Representative sulfonamide-protecting groups include, but are not limited to t-butyl and acyl groups. Exemplary acyl groups include aliphatic lower acyl groups such as the formyl, acetyl, phenylacetyl, butyryl, isobutyryl, valeryl, isovaleryl and pivaloyl groups, and aromatic acyl groups such as the benzoyl and 4-acetoxybenzoyl. Standard deprotection techniques and reagents are used to remove the $P^6$ group, and may vary depending upon which group is used. For example, HCl is commonly used when $P^6$ is t-butyl, while NaOH is commonly used when $P^6$ is an acyl group.

In addition, L is used to designate a "leaving group," a term used herein to mean a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, triflate, tosylate, brosylate, nosylate and the like; and acyloxy groups, such as acetoxy, trifluoroacetoxy and the like.

Suitable bases for use in these schemes include, by way of illustration and not limitation, potassium carbonate, calcium carbonate, sodium carbonate, triethylamine, pyridine, 1,8-diazabicyclo-[5.4.0]undec-7-ene (DBU), N,N-diisopropylethylamine (DIPEA), sodium hydroxide, potassium hydroxide, potassium t-butoxide, and metal hydrides.

Suitable inert diluents or solvents for use in these schemes include, by way of illustration and not limitation, tetrahydrofuran (THF), acetonitrile (MeCN), N,N-dimethylformamide (DMF), dimethyl sulfoxide (DMSO), toluene, dichloromethane (DCM), chloroform ($CHCl_3$), carbon tetrachloride ($CCl_4$), 1,4-dioxane, methanol, ethanol, water, and the like.

Suitable carboxylic acid/amine coupling reagents include benzotriazol-1-yloxytris(dimethylamino)phosphonium hexafluorophosphate (BOP), benzotriazol-1-yloxytripyrrolidinophosphonium hexafluorophosphate (PyBOP), O-(7-azabenzotriazol-1-yl-N,N,N',N'-tetramethyluronium hexafluorophosphate (HATU), dicyclohexylcarbodiimide (DCC), N-(3-dimethylaminopropyl)-N'-ethylcarbodiimide (EDC), carbonyldiimidazole (CDI), and the like. Coupling reactions are conducted in an inert diluent in the presence of a base such as DIPEA, and are performed under conventional amide bond-forming conditions.

All reactions are typically conducted at a temperature within the range of about −78° C. to 100° C., for example at room temperature. Reactions may be monitored by use of thin layer chromatography (TLC), high performance liquid chromatography (HPLC), and/or LCMS until completion. Reactions may be complete in minutes, or may take hours, typically from 1-2 hours and up to 48 hours. Upon completion, the resulting mixture or reaction product may be further treated in order to obtain the desired product. For example, the resulting mixture or reaction product may be subjected to one or more of the following procedures: concentrating or partitioning (for example, between EtOAc and water or between 5% THF in EtOAc and 1M phosphoric acid); extraction (for example, with EtOAc, $CHCl_3$, DCM, chloroform); washing (for example, with saturated aqueous NaCl, saturated $NaHCO_3$, $Na_2CO_3$ (5%), $CHCl_3$ or 1M NaOH); drying (for example, over $MgSO_4$, over $Na_2SO_4$, or in vacuo); filtering; crystallizing (for example, from EtOAc and hexane); being concentrated (for example, in vacuo); and/or purification (e.g., silica gel chromatography, flash chromatography, preparative HPLC, reverse phase-HPLC, or crystallization).

By way of illustration, compounds of formula I, as well as their salts, solvates, and prodrugs can be prepared by coupling a compound of formula 1 with a compound of formula 2:

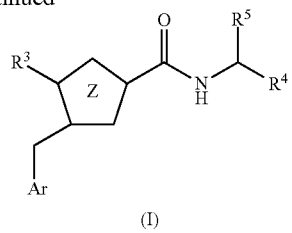

$Ar^*$ represents $Ar\text{—}R^{1*}$, where $R^{1*}$ is $R^1$ or a protected form of $R^1$, for example, -tetrazolyl-BOC or a precursor of $R^1$ such as —CN that is then converted to tetrazolyl. $R^{4*}$ represents $R^4$ or a protected form of $R^4$. Therefore, when $R^{1*}$ represents $R^1$ and $R^{4*}$ represents $R^4$, the reaction is complete after the coupling step.

On the other hand, when $R^{1*}$ represents a protected form of $R^1$ and/or $R^{4*}$ represents a protected form of $R^4$, a subsequent global or sequential deprotection step would yield the non-protected compound. Similarly, when $R^{1*}$ represents a precursor of a subsequent conversion step would yield the desired compound. Reagents and conditions for the deprotection vary with the nature of protecting groups in the compound. Thus, one method of preparing compounds of the invention involves coupling compounds (1) and (2), with an optional deprotection step when $R^{1*}$ is a protected form of $R^1$ and/or $R^{4*}$ is a protected form of $R^4$, thus forming a compound of formula I or a pharmaceutically acceptable salt thereof.

Examples of compound of formula 1 include:
5-propyl-4-[2'-(1H-tetrazol-5-yl)biphenyl-4-ylmethyl]oxazole-2-carboxylic acid;
5-ethoxy-4-[2'-(1H-tetrazol-5-yl)biphenyl-4-ylmethyl]oxazole-2-carboxylic acid;
4-[2-fluoro-2'-(1H-tetrazol-5-yl)biphenyl-4-ylmethyl]-5-propyloxazole-2-carboxylic acid;
4-[2-fluoro-2'-(1H-tetrazol-5-yl)biphenyl-4-ylmethyl]-5-ethoxyoxazole-2-carboxylic acid;
4-[3-fluoro-2'-(1H-tetrazol-5-yl)biphenyl-4-ylmethyl]-5-propyloxazole-2-carboxylic acid;
4-[3-fluoro-2'-(1H-tetrazol-5-yl)biphenyl-4-ylmethyl]-5-ethoxyoxazole-2-carboxylic acid;
4-[3,5-difluoro-2'-(1H-tetrazol-5-yl)biphenyl-4-ylmethyl]-5-propyloxazole-2-carboxylic acid;
4-[3,5-difluoro-2'-(1H-tetrazol-5-yl)biphenyl-4-ylmethyl]-5-ethoxyoxazole-2-carboxylic acid;
4-propyl-5-[2'-(1H-tetrazol-5-yl)biphenyl-4-ylmethyl]oxazole-2-carboxylic acid;
4-ethoxy-5-[2'-(1H-tetrazol-5-yl)biphenyl-4-ylmethyl]oxazole-2-carboxylic acid;
5-[2-fluoro-2'-(1H-tetrazol-5-yl)biphenyl-4-ylmethyl]-4-propyloxazole-2-carboxylic acid;
5-[2-fluoro-2'-(1H-tetrazol-5-yl)biphenyl-4-ylmethyl]-4-ethoxyoxazole-2-carboxylic acid;
5-[3-fluoro-2'-(1H-tetrazol-5-yl)biphenyl-4-ylmethyl]-4-propyloxazole-2-carboxylic acid;
5-[3-fluoro-2'-(1H-tetrazol-5-yl)biphenyl-4-ylmethyl]-4-ethoxyoxazole-2-carboxylic acid;
5-[3,5-difluoro-2'-(1H-tetrazol-5-yl)biphenyl-4-ylmethyl]-4-propyloxazole-2-carboxylic acid;
5-[3,5-difluoro-2'-(1H-tetrazol-5-yl)biphenyl-4-ylmethyl]-4-ethoxyoxazole-2-carboxylic acid;
4-(2'-acetylsulfamoylbiphenyl-4-ylmethyl)-5-propyloxazole-2-carboxylic acid;
4-(2'-acetylsulfamoylbiphenyl-4-ylmethyl)-5-ethoxyoxazole-2-carboxylic acid;
4-[2-fluoro-(2'-acetylsulfamoylbiphenyl-4-ylmethyl)]-5-propyloxazole-2-carboxylic acid;

4-[2-fluoro-(2'-acetylsulfamoylbiphenyl-4-ylmethyl)]-5-ethoxyoxazole-2-carboxylic acid;
4-[3-fluoro-(2'-acetylsulfamoylbiphenyl-4-ylmethyl)]-5-propyloxazole-2-carboxylic acid;
4-[3-fluoro-(2'-ACetylsulfamoylbiphenyl-4-ylmethyl)]-5-ethoxyoxazole-2-carboxylic acid;
4-[3,5-difluoro-(2'-acetylsulfamoylbiphenyl-4-ylmethyl)]-5-propyloxazole-2-carboxylic acid;
4-[3,5-difluoro-(2'-acetylsulfamoylbiphenyl-4-ylmethyl)]-5-ethoxyoxazole-2-carboxylic acid;
5-(2'-acetylsulfamoylbiphenyl-4-ylmethyl)-4-propyloxazole-2-carboxylic acid;
5-(2'-acetylsulfamoylbiphenyl-4-ylmethyl)-4-ethoxyoxazole-2-carboxylic acid;
5-[2-fluoro-(2'-acetylsulfamoylbiphenyl-4-ylmethyl)]-4-propyloxazole-2-carboxylic acid;
5-[2-fluoro-(2'-acetylsulfamoylbiphenyl-4-ylmethyl)]-4-ethoxyoxazole-2-carboxylic acid;
5-[3-fluoro-(2'-acetylsulfamoylbiphenyl-4-ylmethyl)]-4-propyloxazole-2-carboxylic acid;
5-[3-fluoro-2(2'-acetylsulfamoylbiphenyl-4-ylmethyl)]-4-ethoxyoxazole-2-carboxylic acid;
5-[3,5-difluoro-(2'-acetylsulfamoylbiphenyl-4-ylmethyl)]-4-propyloxazole-2-carboxylic acid; and
5-[3,5-difluoro-(2'-acetylsulfamoylbiphenyl-4-ylmethyl)]-4-ethoxyoxazole-2-carboxylic acid.

Examples of compounds of formula 2 include:
(R)-2-((R)-2-amino-3-phenylpropyldisulfanyl)-1-benzylethylamine;
(R)-1-((R)-2-amino-4-methylpentyldisulfanylmethyl)-3-methylbutylamine (dimer);
(R)-3-amino-4-(2-chlorophenyl)butyric acid;
(R)-3-amino-4-(2-bromophenyl)butyric acid;
(R)-3-amino-4-phenylbutyric acid;
(R)-3-amino-4-(2-fluorophenyl)butyric acid;
(R)-3-amino-4-(2-methylphenyl)butyric acid;
(R)-3-amino-4-(2-trifluoromethylphenyl)butyric acid;
(2R,3R)-3-amino-2-hydroxy-4-phenylbutyric acid ethyl ester;
3-amino-4-(2-chlorophenyl)-2-hydroxybutyric acid ethyl ester;
[(S)-1-benzyl-2-(benzyloxyformylamino)ethyl]carbamic acid t-butyl ester;
[1-benzyl-2-hydroxycarbamoylethyl]carbamic acid t-butyl ester;
[1-(2-chlorobenzyl)-2-hydroxycarbamoylethyl]carbamic acid t-butyl ester; and
3-amino-2,N-dihydroxy-4-phenylbutyramide.

Other protected forms, deprotected forms, isomers and racemic mixtures can also be used.

Certain intermediates described herein are believed to be novel and accordingly, such compounds are provided as further aspects of the invention including, for example, the compounds of formulas V, VI and VII, or a salt thereof:

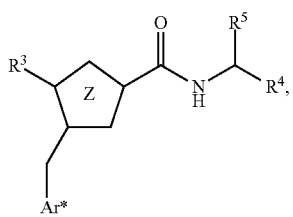

(V)

where Ar* is Ar—R$^{1*}$; Ar, Z, R$^3$, R$^4$, and R$^5$ are as defined for formula I; and R$^{1*}$ is —SO$_2$NH—P$^6$ or tetrazolyl-P$^4$; where P$^4$ is a tetrazole-protecting group and P$^6$ is a sulfonamide-protecting group;

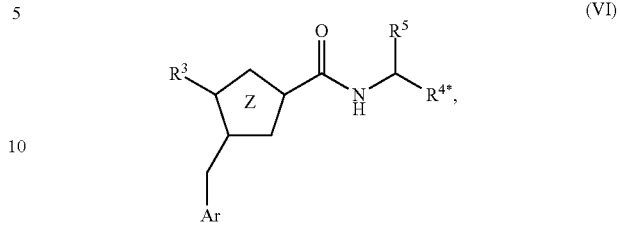

(VI)

where Ar, Z, R$^3$, and R$^5$ are as defined for formula I; R$^{4*}$ is —CH$_2$—S—P$^3$, —CH$_2$—N(O—P$^5$)—C(O)H, —CH(R$^{4b}$)C(O)NH(O—P$^5$), or —CH(R$^{4b}$)COO—P$^2$; and R$^{4b}$ is as defined for formula I; where P$^2$ is a carboxy-protecting group, P$^3$ is a thiol-protecting group, P$^5$ is a hydroxyl-protecting group; and

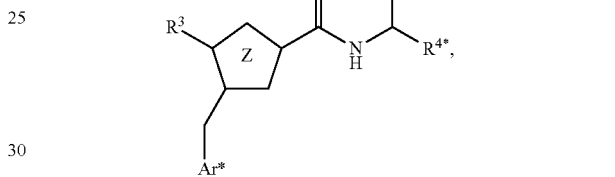

(VII)

where Ar* is Ar—R$^{1*}$; Ar, Z, R$^3$, and R$^5$ are as defined for formula I; R$^{1*}$ is —SO$_2$NH—P$^6$ or tetrazolyl-P$^4$; R$^{4*}$ is —CH$_2$—S—P$^3$, —CH$_2$—N(O—P$^5$)—C(O)H, —CH(R$^{4b}$)C(O)NH(O—P$^5$), or —CH(R$^{4b}$)COO—P$^2$; and R$^{4b}$ is as defined for formula I; where P$^2$ is a carboxy-protecting group, P$^3$ is a thiol-protecting group, P$^4$ is a tetrazole-protecting group, P$^5$ is a hydroxyl-protecting group, and P$^6$ is a sulfonamide-protecting group. Thus, another method of preparing compounds of the invention involves deprotecting a compound of formula V, VI, or VII.

Further details regarding specific reaction conditions and other procedures for preparing representative compounds of the invention or intermediates thereof are described in the Examples set forth below.

UTILITY

Compounds of the invention possess angiotensin II type 1 (AT$_1$) receptor antagonist activity. In one embodiment, compounds of the invention are selective for inhibition of the AT$_1$ receptor over the AT$_2$ receptor. Compounds of the invention also possess neprilysin (NEP) inhibition activity, that is, the compounds are able to inhibit enzyme-substrate activity. In another embodiment, the compounds do not exhibit significant inhibitory activity of the angiotensin-converting enzyme. Compounds of formula I may be active drugs as well as prodrugs. Thus, when discussing the activity of compounds of the invention, it is understood that any such prodrugs have the expected activity once metabolized.

One measure of the affinity of a compound for the AT$_1$ receptor is the inhibitory constant (K$_i$) for binding to the AT$_1$ receptor. The pK$_i$ value is the negative logarithm to base 10 of the K$_i$. One measure of the ability of a compound to inhibit NEP activity is the inhibitory concentration (IC$_{50}$), which is the concentration of compound that results in half-maximal inhibition of substrate conversion by the NEP enzyme. The $pIC_{50}$ value is the negative logarithm to base 10 of the $IC_{50}$. Compounds of the invention that have both $AT_1$ receptor-antagonizing activity and NEP enzyme-inhibiting activity are of particular interest, including those that exhibit a $pk_i$ at the $AT_1$ receptor greater than or equal to about 5.0, and exhibit a $pIC_{50}$ for NEP greater than or equal to about 5.0.

In one embodiment, compounds of interest have a $pK_i$ at the $AT_1$ receptor≥about 6.0, a $pK_i$ at the $AT_1$ receptor≤about 7.0, or a $pK_i$ at the $AT_1$ receptor≥about 8.0. Compounds of interest also include those having a $pIC_{50}$ for NEP≥about 6.0 or a $pIC_{50}$ for NEP≥about 7.0. In another embodiment, compounds of interest have a $pK_i$ at the $AT_1$ receptor within the range of about 8.0-10.0 and a $pIC_{50}$ for NEP within the range of about 7.0-10.0.

In another embodiment, compounds of particular interest have a $pK_i$ for binding to an $AT_1$ receptor greater than or equal to about 7.5 and a NEP enzyme $pIC_{50}$ greater than or equal to about 7.0. In another embodiment, compounds of interest have a $pK_i$ greater than or equal to about 8.0 and a $pIC_{50}$ greater than or equal to about 8.0.

It is noted that in some cases, compounds of the invention, while still having dual activity, may possess either weak $AT_1$ receptor antagonist activity or weak NEP inhibition activity. In such cases, those of skill in the art will recognize that these compounds still have utility as primarily either a NEP inhibitor or a $AT_1$ receptor antagonist, respectively, or have utility as research tools.

Exemplary assays to determine properties of compounds of the invention, such as the $AT_1$ receptor binding and/or NEP inhibiting activity, are described in the Examples and include by way of illustration and not limitation, assays that measure $AT_1$ and $AT_2$ binding (described in Assay 1), and NEP inhibition (described in Assay 2). Useful secondary assays include assays to measure ACE inhibition (also described in Assay 2) and aminopeptidase P (APP) inhibition (described in Sulpizio et al. (2005) *JPET* 315:1306-1313). A pharmacodynamic assay to assess the in vivo inhibitory potencies for ACE, $AT_1$, and NEP in anesthetized rats is described in Assay 3 (see also Seymour et al. (1985) *Hypertension* 7(Suppl I):I-35-I-42 and Wigle et al. (1992) *Can. J. Physiol. Pharmacol.* 70:1525-1528), where $AT_1$ inhibition is measured as the percent inhibition of the angiotensin II pressor response, ACE inhibition is measured as the percent inhibition of the angiotensin I pressor response, and NEP inhibition is measured as increased urinary cyclic guanosine 3',5'-monophosphate (cGMP) output. Useful in vivo assays include the conscious spontaneously hypertensive rat (SHR) model, which is a renin dependent hypertension model that is useful for measuring $AT_1$ receptor blocking (described in Assay 4; see also Intengan et al. (1999) *Circulation* 100(22):2267-2275 and Badyal et al. (2003) *Indian Journal of Pharmacology* 35:349-362), and the conscious desoxycorticosterone acetate-salt (DOCA-salt) rat model, which is a volume dependent hypertension model that is useful for measuring NEP activity (described in Assay 5; see also Trapani et al. (1989) *J. Cardiovasc. Pharmacol.* 14:419-424, Intengan et al. (1999) *Hypertension* 34(4):907-913, and Badyal et al. (2003) supra). Both the SHR and DOCA-salt models are useful for evaluating the ability of a test compound to reduce blood pressure. The DOCA-salt model is also useful to measure a test compound's ability to prevent or delay a rise in blood pressure. Compounds of the invention are expected to antagonize the $AT_1$ receptor and/or inhibit the NEP enzyme in any of the assays listed above, or assays of a similar nature. Thus, the aforementioned assays are useful in determining the therapeutic utility of compounds of the invention, for example, their utility as antihypertensive agents. Other properties and utilities of compounds of the invention can be demonstrated using other in vitro and in vivo assays well-known to those skilled in the art.

Compounds of the invention are expected to be useful for the treatment and/or prevention of medical conditions responsive to $AT_1$ receptor antagonism and/or NEP inhibition. Thus it is expected that patients suffering from a disease or disorder that is treated by antagonizing the $AT_1$ receptor and/or by inhibiting the NEP enzyme can be treated by administering a therapeutically effective amount of a compound of the invention. For example, by antagonizing the $AT_1$ receptor and thus interfering with the action of angiotensin II on its receptors, these compounds are expected to find utility in preventing the increase in blood pressure produced by angiotensin II, a potent vasopressor. In addition, by inhibiting NEP, the compounds are also expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. For example, by potentiating the effects of the natriuretic peptides, compounds of the invention are expected to be useful to treat glaucoma. These compounds are also expected to have other physiological actions, for example, on the renal, central nervous, reproductive and gastrointestinal systems.

Compounds of the invention are expected to find utility in treating and/or preventing medical conditions such as cardiovascular and renal diseases. Cardiovascular diseases of particular interest include heart failure such as congestive heart failure, acute heart failure, chronic heart failure, and acute and chronic decompensated heart failure. Renal diseases of particular interest include diabetic nephropathy and chronic kidney disease. One embodiment of the invention relates to a method for treating hypertension, comprising administering to a patient a therapeutically effective amount of a compound of the invention. Typically, the therapeutically effective amount is the amount that is sufficient to lower the patient's blood pressure. In one embodiment, the compound is administered as an oral dosage form.

Another embodiment of the invention relates to a method for treating heart failure, comprising administering to a patient a therapeutically effective amount of a compound of the invention. Typically, the therapeutically effective amount is the amount that is sufficient to lower blood pressure and/or improve renal functions. In one embodiment, the compound is administered as an intravenous dosage form. When used to treat heart failure, the compound may be administered in combination with other therapeutic agents such as diuretics, natriuretic peptides, and adenosine receptor antagonists.

Compounds of the invention are also expected to be useful in preventative therapy, for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

In addition, as NEP inhibitors, compounds of the invention are expected to inhibit enkephalinase, which will inhibit the degradation of endogenous enkephalins and thus such compounds may also find utility as analgesics. Due to their NEP inhibition properties, compounds of the invention are also expected to be useful as antitussive agents and antidiarrheal agents (for example, for the treatment of watery diarrhea), as well as find utility in the treatment of menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, the compounds of the invention are expected to be useful in treating female sexual dysfunction, which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, compounds of the invention may be combined with one or more of the following secondary agents: PDE5 inhibitors, dopamine agonists, estrogen receptor agonists and/or antagonists, androgens, and estrogens.

The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Since compounds of the invention possess $AT_1$ receptor antagonist activity and/or NEP enzyme inhibition activity, such compounds are also useful as research tools for investigating or studying biological systems or samples having $AT_1$ receptors or a NEP enzyme, for example to study diseases where the $AT_1$ receptor or NEP enzyme plays a role. Any suitable biological system or sample having $AT_1$ receptors and/or a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention an $AT_1$ receptor in a mammal is antagonized by administering an $AT_1$-antagonizing amount of a compound of the invention. In another particular embodiment, NEP enzyme activity in a mammal is inhibited by administering a NEP-inhibiting amount of a compound of the invention. Compounds of the invention can also be used as research tools by conducting biological assays using such compounds.

When used as a research tool, a biological system or sample comprising an $AT_1$ receptor and/or a NEP enzyme is typically contacted with an $AT_1$ receptor-antagonizing or NEP enzyme-inhibiting amount of a compound of the invention. After the biological system or sample is exposed to the compound, the effects of antagonizing the $AT_1$ receptor and/or inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., i.v. or s.c. administration, and so forth. This determining step can involve measuring a response (a quantitative analysis) or can involve making an observation (a qualitative analysis). Measuring a response involves, for example, determining the effects of the compound on the biological system or sample using conventional procedures and equipment, such as radioligand binding assays and measuring ligand-mediated changes in functional assays. The assay results can be used to determine the activity level as well as the amount of compound necessary to achieve the desired result, that is, an $AT_1$ receptor-antagonizing and/or a NEP enzyme-inhibiting amount. Typically, the determining step will involve determining the $AT_1$ receptor ligand-mediated effects and/or determining the effects of inhibiting the NEP enzyme.

Additionally, compounds of the invention can be used as research tools for evaluating other chemical compounds, and thus are also useful in screening assays to discover, for example, new compounds having $AT_1$ receptor-antagonizing activity and/or NEP-inhibiting activity. In this manner, a compound of the invention is used as a standard in an assay to allow comparison of the results obtained with a test compound and with compounds of the invention to identify those test compounds that have about equal or superior activity, if any. For example, $K_i$ data (as determined, for example, by a binding assay) for a test compound or a group of test compounds is compared to the $K_i$ data for a compound of the invention to identify those test compounds that have the desired properties, for example, test compounds having a $K_i$ value about equal or superior to a compound of the invention, if any. This aspect of the invention includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include an $AT_1$ receptor binding assay and a NEP enzyme inhibition assay.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, the compounds of the invention may be administered, for example orally, in multiple doses per day (for example, two, three, or four times daily), in a single daily dose or a single weekly dose. It will be understood that any form of the compounds of the invention, (that is, free base, free acid, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts, solvates and prodrugs of that compound.

The pharmaceutical compositions of the invention typically contain a therapeutically effective amount of a compound of the invention. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy,* 20$^{th}$ Edition, Lippincott Williams & White, Baltimore, Md. (2000); and H. C. Ansel et al., *Pharmaceutical Dosage Forms and Drug Delivery Systems,* 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In formulations where the compound of the invention contains a thiol group, additional consideration may be given to minimize or eliminate oxidation of the thiol to form a disulfide. In solid formulations, this may be accomplished by reducing the drying time, decreasing the moisture content of the formulation, and including materials such as ascorbic acid, sodium ascorbate, sodium sulfite and sodium bisulfate, as well as materials such as a mixture of lactose and microcrystalline cellulose. In liquid formulations, stability of the thiol may be improved by the addition of amino acids, antioxidants, or a combination of disodium edetate and ascorbic acid.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agaragar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metalchelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, optionally with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (for example, by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages, or dimerization of thiols that may be present in the compound. These formulations may be rendered sterile by use of a sterile injectable medium, a sterilizing agent, filtration, irradiation, or heat. In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by a linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin. Exemplary buffers for such formulations include carboxylic acid-based buffers such as citrate, lactate and maleate buffer solutions.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the compounds of the invention may be administered in combination with one or more other therapeutic agents. Thus, in one embodiment, pharmaceutical compositions of the invention contain other drugs that are co-administered with a compound of the invention. For example, the composition may further comprise one or more drugs (also referred to as "secondary agents(s)") selected from the group of diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, and combinations thereof. Such therapeutic agents are well known in the art, and specific examples are described herein. By combining a compound of the invention with a secondary agent, triple therapy can be achieved; $AT_1$ receptor antagonist activity, NEP inhibition activity, and activity associated with the secondary agent (for example, $\beta_1$ adrenergic receptor blocker) can be achieved using only two active components. Since compositions containing two active components are typically easier to formulate than compositions containing three active components, such two-component compositions provide a significant advantage over compositions containing three active components. Accordingly, in yet another aspect of the invention, a pharmaceutical composition comprises a compound of the invention, a second active agent, and a pharmaceutically acceptable carrier. Third, fourth etc. active agents may also be included in the composition. In combination therapy, the amount of compound of the invention that is administered, as well as the amount of secondary agents, may be less than the amount typically administered in monotherapy.

Compounds of the invention may be physically mixed with the second active agent to form a composition containing both agents; or each agent may be present in separate and distinct compositions which are administered to the patient simultaneously or at separate times. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, a compound of the invention can be orally administered simultaneously or sequentially with another active agent using two tablets, with one tablet for each active agent, where sequential may mean being administered immediately after administration of the compound of the invention or at some predetermined time later (for example, one hour later or three hours later). Alternatively, the combination may be administered by different routes of administration, that is, one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc,) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with a compound of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, a compound of the invention is administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosemide, bumetanide, butazolamide, chloraminophenamide, clofenamide, clopamide, clorexolone, disulfamide, ethoxolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compounds of the invention may also be administered in combination with a $\beta_1$ adrenergic receptor blocker. Representative $\beta_1$ adrenergic receptor blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$ adrenergic receptor blocker is selected from atenolol, bisoprolol, metoprolol, propranolol, sotalol, and combinations thereof.

In one embodiment, a compound of the invention is administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexyline, prenylamine, ryosidine, scmotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof.

Compounds of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltopril, pentopril, perindopril, quinapril, quinaprilat, ramipril, ramipril at, saralasin acetate, spirapril, temocapril, trandolapril, zofenopril, and combinations thereof. In a particular embodiment, the ACE inhibitor is selected from: benazepril, enalapril, lisinopril, ramipril, and combinations thereof.

In one embodiment, a compound of the invention is administered in combination with an $AT_1$ receptor antagonist, also known as angiotensin II type 1 receptor blockers (ARBs). Representative ARBs include, but are not limited to, abitesartan, benzyllosartan, candesartan, candesartan cilexetil, elisartan, embusartan, enoltasosartan, eprosartan, fonsartan, forasartan, glycyllosartan, irbesartan, isoteoline, losartan, medoximil, milfasartan, olmesartan, opomisartan, pratosartan, ripisartan, saprisartan, saralasin, sarmesin, tasosartan, telmisartan, valsartan, zolasartan, and combinations thereof. In a particular embodiment, the ARB is selected from candesartan, eprosartan, irbesartan, losartan, olmesartan, irbesartan, saprisartan, tasosartan, telmisartan, and combinations thereof. Exemplary salts include eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

In another embodiment, a compound of the invention is administered in combination with a neprilysin (NEP) inhibitor. Representative NEP inhibitors include, but are not limited to: candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2 (S)-ylcarbonyl]-4 (R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl)propionamide); SCH-32615 ((S)—N—[N-(1-carboxy-2-phenylethyl)-L-phenylalanyl]-β-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl)propionyl]-L-methionine ethyl ester); spinorphin; SQ-28132 (N-[2-(mercaptomethyl)-1-oxo-3-phenylpropyl] leucine); SQ-28603 (N-[2-(mercaptomethyl)-1-oxo-3-phenylpropyl]-(3-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino]cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl] cyclopentyl}propionic acid); 5-biphenyl-4-yl-4-(3-carboxypropionylamino)-2-methylpentanoic acid and 5-biphenyl-4-yl-4-(3-carboxypropionylamino)-2-methylpentanoic acid ethyl ester (WO 2007/056546); daglutril [(3S, 2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from candoxatril, candoxatrilat, CGS-24128, phosphoramidon, SCH-32615, SCH-34826, SQ-28603, thiorphan, and combinations thereof. The NEP inhibitor will be administered in an amount sufficient to provide from about 20-800 mg per day, with typical daily dosages ranging from 50-700 mg per day, more commonly 100-600 or 100-300 mg per day.

In yet another embodiment, a compound of the invention is administered in combination with a non-steroidal anti-inflammatory agent (NSAID). Representative NSAIDs include, but are not limited to: acemetacin, acetyl salicylic acid, alclofenac, alminoprofen, amfenac, amiprilose, amoxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxcpac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In yet another embodiment, a compound of the invention is administered in combination with an anti-lipid agent. Representative anti-lipid agents include, but are not limited to, statins such as atorvastatin, fluvastatin, lovastatin, pravastatin, rosuvastatin and simvastatin; cholesteryl ester transfer proteins (CETPs); and combinations thereof.

In yet another embodiment, a compound of the invention is administered in combination with an anti-diabetic agent. Representative anti-diabetic agents include injectable drugs as well as orally effective drugs, and combinations thereof. Examples of injectable drugs include, but are not limited to, insulin and insulin derivatives. Examples of orally effective drugs include, but are not limited to: biguanides such as metformin; glucagon antagonists; α-glucosidase inhibitors such as acarbose and miglitol; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In one embodiment, a compound of the invention is administered in combination with an anti-thrombotic agent. Representative anti-thrombotic agents include, but are not limited to, aspirin, anti-platelet agents, heparin, and combinations thereof. Compounds of the invention may also be administered in combination with a renin inhibitor, examples of which include, but are not limited to, aliskiren, enalkiren, remikiren, and combinations thereof. In another embodiment, a compound of the invention is administered in combination with an endothelin receptor antagonist, representative examples of which include, but are not limited to, bosentan, darusentan, tezosentan, and combinations thereof. Compounds of the invention may also be administered in combination with an endothelin converting enzyme inhibitor, examples of which include, but are not limited to, phosphoramidon, CGS 26303, and combinations thereof. In yet another embodiment, a compound of the invention is administered in combination with an aldosterone antagonist, representative examples of which include, but are not limited to, eplerenone, spironolactone, and combinations thereof.

Combined therapeutic agents may also be helpful in further combination therapy with compounds of the invention. For example, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with the compounds of the invention. Dual-acting agents may also be helpful in combination therapy with compounds of the invention. For example, angiotensin-converting enzyme/neprilysin (ACE/NEP) inhibitors such as: AVE-0848 ((4S,7S,12bR)-7-[3-methyl-2(S)-sulfanylbutyramido]-6-oxo-1,2,3,4,6,7,8,12b-octahydropyrido[2,1-a][2]benzazepine-4-carboxylic acid); AVE-7688 (ilepatril) and its parent compound; BMS-182657 (2-[2-oxo-3(S)-[3-phenyl-2(S)-sulfanylpropionamido]-2,3,4,5-tetrahydro-1H-1-benzazepin-1-yl]acetic acid); CGS-26303 ([N-[2-(biphenyl-4-yl)-1(S)-(1H-tetrazol-5-yl)ethyl]amino]methylphosphonic acid); CGS-35601 (N-[1-[4-methyl-2(S)-sulfanylpentanamido]cyclopentylcarbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4α,7α(R*),12bβ]]-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2(S)-(mercaptomethyl)-3(R)-phenylbutyl]-L-alanine); sampatrilat; SA-898 ((2R,4R)—N-[2-(2-hydroxyphenyl)-3-(3-mercaptopropionyl) thiazolidin-4-ylcarbonyl]-L-phenylalanine); Sch-50690 (N-[1(S)-carboxy-2-[N2-(methanesulfonyl)-L-lysylamino] ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine. Exemplary vasopressin receptor antagonists include tolvaptan.

The following formulations illustrate representative pharmaceutical compositions of the invention.

Exemplary Hard Gelatin Capsules for Oral Administration

A compound of the invention (50 g), 440 g spray-dried lactose and 10 g magnesium stearate are thoroughly blended. The resulting composition is then loaded into hard gelatin capsules (500 mg of composition per capsule). Alternately, a compound of the invention (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Exemplary Gelatin Capsule Formulation for Oral Administration

A compound of the invention (100 mg) is thoroughly blended with polyoxyethylene sorbitan monooleate (50 mg) and starch powder (250 mg). The mixture is then loaded into a gelatin capsule (300 mg of composition per capsule).

Alternately, a compound of the invention (40 mg) is thoroughly blended with microcrystalline cellulose (Avicel PH 103; 260 mg) and magnesium stearate (0.8 mg). The mixture is then loaded into a gelatin capsule (Size #1, White, Opaque) (300 mg of composition per capsule).

Exemplary Tablet Formulation for Oral Administration

A compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a compound of the invention (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a compound of the invention (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, a compound of the invention (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are then admixed with the gelatin formulation, granulated and the resulting mixture compressed to form tablets (100 mg of the compound of the invention per tablet).

Exemplary Suspension Formulation for Oral Administration

The following ingredients are mixed to form a suspension containing 100 mg of the compound of the invention per 10 mL of suspension:

| Ingredients | Amount |
| --- | --- |
| Compound of the invention | 1.0 g |
| Fumaric acid | 0.5 g |

-continued

| Ingredients | Amount |
|---|---|
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Liquid Formulation for Oral Administration

A suitable liquid formulation is one with a carboxylic acid-based buffer such as citrate, lactate and maleate buffer solutions. For example, a compound of the invention (which may be pre-mixed with DMSO) is blended with a 100 mM ammonium citrate buffer and the pH adjusted to pH 5, or is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% $NaHCO_3$ solution, with or without cyclodextrin.

Exemplary Injectable Formulation for Administration by Injection

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

A compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, a compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1 N NaOH. The solution is administered using a nebulizer device that provides about 10 μg to about 500 μg of the compound of the invention per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning.

ACE angiotensin converting enzyme
AcOH acetic acid
APP aminopeptidase P
$AT_1$ angiotensin II type 1 (receptor)
$AT_2$ angiotensin II type 2 (receptor)
BSA bovine serum albumin
DCM dichloromethane or methylene chloride
DIPEA N,N-diisopropylethylamine
DMF N,N-dimethylformamide
DMSO dimethyl sulfoxide
Dnp 2,4-dinitrophenyl
DOCA deoxycorticosterone acetate
EDC N-(3-dimethylaminopropyl)-N'-ethylcarbodiimide hydrochloride
EDTA ethylenediaminetetraacetic acid
EtOAc ethyl acetate
HATU N,N,N',N'-tetramethyl-O-(7-azabenzotriazol-1-yl) uronium hexafluorophosphate
HOBt 1-hydroxybenzotriazole hydrate
LiHMDS lithium hexamethyl disilazide
Mca (7-methoxycoumarin-4-yl)acyl
MeCN acetonitrile
MeOH methanol
NBS N-bromosuccinimide
NEP neprilysin (EC 3.4.24.11)
PBS phosphate buffered saline
SHR spontaneously hypertensive rat
TFA trifluoroacetic acid
THF tetrahydrofuran
Tris tris(hydroxymethyl)aminomethane
Tween-20 polyethylene glycol sorbitan monolaurate Unless noted otherwise, all materials, such as reagents, starting materials and solvents, were purchased from commercial suppliers (such as Sigma-Aldrich, Fluka Riedel-de Haën, and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% $H_2O$/2% MeCN/1.0 mL/L TFA; solvent B was 90% MeCN/10% $H_2O$/1.0 mL/L TFA.

Reactions were worked up as described specifically in each preparation or example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers were done by Nuclear Overhauser effect spectroscopy (NOE). Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Preparation 1

2-(1-Trityl-1H-tetrazol-5-yl)phenylboronic Acid

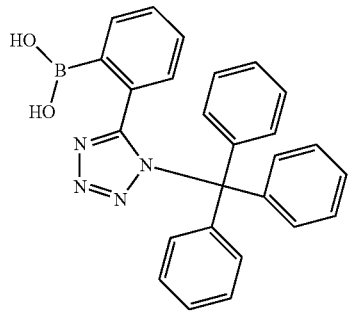 [SMILES: OB(O)c1ccccc1-c1nnnn1C(c1ccccc1)(c1ccccc1)c1ccccc1]

A solution of benzonitrile (60.0 g, 581.9 mmol, 1.0 equiv) in DMF (anhydrous) (600 mL) was placed in a flask that had been purged and maintained with an inert atmosphere of nitrogen. Ammonium chloride (40.5 g, 757.2 mmol, 1.3 equiv) was added, followed by the addition of lithium chloride (2.0 g, 47.2 mmol, 0.1 equiv). To the mixture was added azidosodium (49.4 g, 756.8 mmol, 1.3 equiv). The resulting solution was stirred overnight, while maintaining the temperature at 100° C. The solids were filtered out and washed with EtOAc. The filtrates were combined and concentrated in vacuo. The residue was dissolved in a 10% NaOH aqueous solution (350 ml). The resulting solution was extracted with EtOAc (100 mL) and the aqueous layers were combined. The pH value of the solution was adjusted to 2 with concentrated HCl. The solids were filtered out and dried over reduced pressure to yield 5-phenyl-1H-tetrazole (78.0 g) as a white solid.

ES m/z: [M+H]$^+$ calcd for C$_7$H$_6$N$_4$, 147.1. found 147.1.

A solution of the tetrazole (50.0 g, 342.1 mmol, 1.0 equiv) in DCM (dried) (150 mL) was placed in a flask that had been purged and maintained with an inert atmosphere of nitrogen. Triethylamine (45.0 g, 444.7 mmol, 1.30 equiv) at 0° C. was added to the mixture, followed by the addition of chlorotriphenylmethane (100.0 g, 358.7 mmol, 1.1 equiv) in several batches at 0° C. The resulting solution was stirred for 3 hours at room temperature. The solids were collected by filtration, and the filtrate cake was washed with cold EtOAc (1×100 mL) and water (3×300 mL). The solids were dried under reduced pressure to yield 5-phenyl-1-trityl-1H-tetrazole (125 g) as a white solid. ES m/z: [M+H]+ calcd for C$_{26}$H$_{20}$N$_4$, 389.1. found 389.1.

A solution of the protected tetrazole (70.0 g, 180.2 mmol, 1.0 equiv) in THF (dried) (560 mL) was placed in a flask that had been purged and maintained with an inert atmosphere of nitrogen. The mixture was cooled to −25° C. Butyllithium was added to quench the trace of water in the reaction mixture until the color of the mixture remained red for at least 5 minutes. Butyllithium (80.0 mL, 2.5 mol/L) was then added dropwise to the mixture over a period of about 40 minutes at a temperature below −25° C. The temperature of the mixture was raised to −5° C., and the mixture was stirred at −5° C. for 3 hours. The mixture was then cooled to −25° C. and triisopropyl borate (50.8 g, 270.1 mmol, 1.5 equiv) was added dropwise. The mixture was warmed to temperature in the range of 25-35° C. and stirred for 2 hours. The mixture was cooled again in the range of 0-5° C., and 3% aqueous AcOH (470 mL) was slowly added over 30-40 minutes. The mixture was stirred for 30-40 minutes and then filtered. The crude product was washed with water (2×300 mL) and dried over reduced pressure. The crude product was then purified by recrystallization from EtOAc (1 g/15 ml) to yield the title compound (54 g) as a white solid.

ES m/z: [M+H]$^+$ calcd for C$_{26}$H$_{21}$BN$_4$O$_2$, 433.1. found 433.1.

$^1$H-NMR (400 MHz, DMSO, 400 ppm): δ(ppm)=7.96 (br, 2H), 7.84-7.86 (m, 1H), 7.51-7.53 (m, 1H), 7.44-7.47 (m, 2H), 7.39-7.41 (m, 9H), 7.08-7.10 (m, 6H).

Preparation 2

(Tetrazol-5-yl)phenylboronic Acid

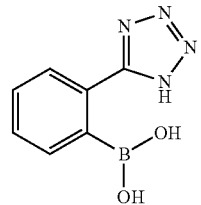 [SMILES: OB(O)c1ccccc1-c1nnn[nH]1]

2-(1-Trityl-1H-tetrazol-5-yl)phenylboronic acid (11.5 g, 26.6 mmol) was combined with 1,4-dioxane (41.5 mL, 532.1 mmol) and 4 M of HCl in 1,4-dioxane (13.3 mL, 53.2 mmol). The mixture was stirred for 2 hours. EtOAc (100 mL) was added. 10 M NaOH was added until pH~9, with constant stirring. The organic layer was extracted and discarded. The aqueous layer was acidified to pH~2 with DCM (10 mL). The product crashed out and was filtered and dried to obtain the title compound (3.5 g) as a white solid.

Preparation 3

4-(4-Bromobenzyl)-5-propyloxazole-2-carboxylic Acid Methyl Ester

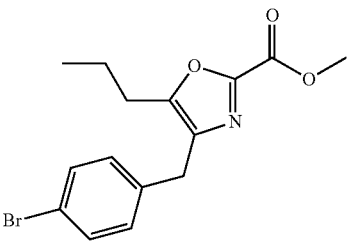 [SMILES: CCCc1oc(C(=O)OC)nc1Cc1ccc(Br)cc1]

A solution of t-butyl 2-aminoacetate (113.7 g, 866.8 mmol, 1.0 equiv) in toluene (1000 mL) was combined with benzophenone (157.9 g, 866.5 mmol, 1.0 equiv) and 4-methylbenzenesulfonic acid (14.9 g, 86.5 mmol, 0.1 equiv). The resulting solution was heated to reflux overnight. The mixture was then concentrated in vacuo to 600 mL. The mixture was cooled to 15° C. with a water/ice bath. The product precipitated and the solids were collected by filtration. The solids was washed with petroleum ether (5×150 mL) to yield t-butyl 2-(diphenylmethyleneamino)acetate (125 g) as a white solid.

A solution of the acetate (80 g, 265.4 mmol, 1.0 equiv) in THF (500 mL) was placed in a flask that had been purged and maintained under nitrogen. This was followed by the addition of LiHMDS (268.3 mL, 1.1 equiv, 1.1 M) dropwise with stirring at −30° C. The resulting solution was stirred for 4 hours at −30~0° C. in a liquid nitrogen bath. To this was added a solution of 1-bromo-4-(bromomethyl)benzene (67.7 g, 270.9 mmol, 1.0 equiv) in THF (200 mL) dropwise with stirring at −30° C. The resulting solution was stirred for an additional 1 hour at room temperature. The reaction was then quenched by the addition of water (500 mL). The resulting solution was extracted with EtOAc and the organic layers combined. The resulting mixture was washed with saturated aqueous NaCl (2×300 mL). The mixture was dried over anhydrous $Na_2SO_4$ and concentrated in vacuo to yield t-butyl 3-(4-bromophenyl)-2-(diphenylmethyleneamino)propanoate (115 g) as a yellow solid. A solution of this solid (115 g, 148.6 mmol, 1.0 equiv) in $HCl/H_2O$ (6N) (300 mL) was heated to reflux overnight. The resulting mixture was concentrated in vacuo and the crude product was washed with EtOAc to yield 2-amino-3-(4-bromophenyl)-propanoic acid hydrochloride (52.7 g) as a white solid.

A solution of the propanoic acid hydrochloride (52.7 g, 140.9 mmol, 1.0 equiv) in THF (200 mL) was combined with a solution of NaOH (15 g, 375.0 mmol, 2.0 equiv) in water (200 mL), and $(Boc)_2O$ (43 g, 197.0 mmol, 1.1 equiv). The resulting solution was stirred overnight at room temperature. The mixture was then concentrated in vacuo and the pH adjusted to 5 with AcOH. The resulting solution was extracted with EtOAc and the organic layers combined. The resulting mixture was washed with water (1×300 mL) and saturated aqueous NaCl (1×300 mL), then concentrated in vacuo. The crude product was washed with petroleum ether to yield 3-(4-bromophenyl)-2-(tert-butoxycarbonyl)propanoic acid (45 g).

$^1$H-NMR (300 MHz, $CDCl_3$): δ(ppm)=8.37 (1H, s), 7.45 (2H, d, J=5 Hz), 7.08 (2H, d, J=9 Hz), 4.97 (1H, d), 4.62 (1H, m), 3.02-3.22 (2H, d), 1.40 (9H, s).

A solution of the propanoic acid (45 g, 117.7 mmol, 1.0 equiv) in DCM (400 mL) was combined with N-methoxymethanamine hydrochloride (15.3 g, 156.9 mmol, 1.2 equiv), EDC.HCl (30.1 g, 157.0 mmol, 1.2 equiv), HOBT (21.2 g, 156.9 mmol, 1.2 equiv), and triethylamine (30 mL). The resulting solution was stirred overnight at room temperature. The reaction was then quenched by the addition of water (300 mL). The resulting mixture was washed with 2M citric acid (2×200 mL) and saturated $NaHCO_3$ (1×200 mL), then dried over anhydrous $MgSO_4$ and concentrated in vacuo to yield t-butyl 3-(4-bromophenyl)-1-(methoxy(methyl)amino)-1-oxopropan-2-ylcarbamate (26 g) as a white solid.

A solution of propylmagnesium bromide (29.7 g, 201.6 mmol, 3.0 equiv) in THF (200 mL) was added dropwise with stirring at 0° C. to a solution of the carbamate (26 g, 66.5 mmol, 1.0 equiv) in THF (200 mL). The resulting solution was stirred overnight at room temperature. The reaction was then quenched by the addition of aqueous $NH_4Cl$ (200 mL). The resulting solution was extracted with EtOAc and the organic layers combined. The resulting mixture was washed with saturated $NaHCO_3$ (200 mL) and saturated aqueous NaCl (200 mL), then dried over anhydrous $MgSO_4$. The residue was applied onto a silica gel column with petroleum ether/EtOAc (5:1) to yield t-butyl 1-(4-bromophenyl)-3-oxohexan-2-ylcarbamate (14 g) as a white solid.

$^1$H-NMR (300 MHz, $CDCl_3$): δ(ppm)=7.43 (2H, d, J=6 Hz), 7.04 (2H, d, J=9 Hz), 5.13 (1H, d), 4.53 (1H, m), 2.87-3.11 (2H, d), 2.42 (2H, t), 1.59 (2H, m), 1.43 (9H, s), 0.9 (3H, t)

A solution of the carbamate (8.0 g, 21.2 mmol, 1.0 equiv) in ether (100 mL) was placed in a flask, and HCL gas was introduced for 5 hours at room temperature. The resulting mixture was concentrated in vacuo to yield crude 2-amino-1-(4-bromophenyl)hexan-3-one hydrochloride (7.2 g) as a white solid. A solution of this solid (7.2 g, 1.0 equiv) in THF (100 mL) and methyl 2-chloro-2-oxoacetate (2.9 g, 1.0 equiv) was combined with triethylamine (4.7 g, 2.0 equiv), which was added dropwise with stirring. The resulting solution was stirred overnight at room temperature. The reaction was then quenched by the addition of water (200 mL). The resulting solution was extracted with EtOAc and the organic layers combined. The resulting mixture was washed with saturated aqueous NaCl (1×100 mL) and dried over $Na_2SO_4$. The residue was applied onto a silica gel column with petroleum ether/EtOAc (5:1) to yield methyl 2-(1-(4-bromophenyl)-3-oxohexan-2-ylamino)-2-oxoacetate (4.7 g) as a white solid.

A solution of the oxoacetate (4.7 g, 13.0 mmol, 1.0 equiv) in phosphoryl trichloride (30.3 g) was stirred for 2 hours at 130° C. in an oil bath. The reaction was then quenched by the addition of water/ice (100 mL). The pH was adjusted to 9 with sodium bicarbonate. The resulting solution was extracted with EtOAc and the organic layers combined. The resulting mixture was washed with saturated aqueous NaCl (2×200 mL), dried over anhydrous $Na_2SO_4$, and concentrated in vacuo. The residue was applied onto a silica gel column with EtOAc/petroleum ether (1:10) to yield the title compound (3.2 g) as a light yellow solid. ES m/z: [M+H]$^+$ 339.

$^1$H-NMR (300 MHz, $CDCl_3$): δ(ppm)=7.42 (2H, dd, J=3.3 Hz), 7.12 (2H, d, J=9 Hz), 3.96 (3H, s), 3.86 (2H, s), 2.64 (2H, t), 1.67 (2H, m), 0.91 (3H, t)

Preparation 4

5-Propyl-4-[2'-(1H-tetrazol-5-yl)biphenyl-4-ylmethyl]oxazole-2-carboxylic Acid

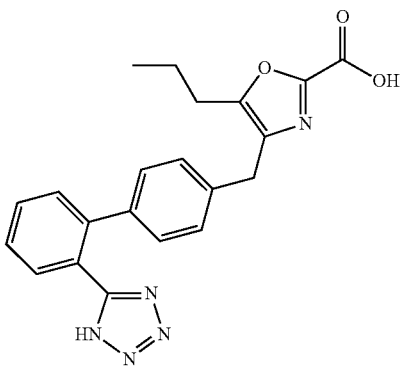 [SMILES: CCCc1oc(C(=O)O)nc1Cc1ccc(-c2ccccc2-c2nnn[nH]2)cc1]

A solution of 4-(4-bromobenzyl)-5-propyloxazole-2-carboxylic acid methyl ester (500.0 mg, 1474 mmol), (tetrazol- 5-yl)phenylboronic acid (336 mg, 1.8 mmol), tetrakis(triphenylphosphine)palladium(0) (85.2 mg, 73.7 μmol), 1 M NaOH in water (4.7 mL, 4.7 mmol), and MeOH (7.2 mL, 177 mmol) was heated at 90° C. for 2 hours in the microwave. 6M aqueous HCl was added until pH 7 was achieved. The mixture was concentrated in vacuo. The concentrate was extracted with EtOAc (2×15 mL) and 1M aqueous HCl (10 mL). The combined organic extracts were dried over $Na_2SO_4$, filtered and concentrated in vacuo to yield the title compound (540 mg).

Compounds such as 5-ethoxy-4-[2'-(1H-tetrazol-5-yl)biphenyl-4-ylmethyl]oxazole-2-carboxylic acid, as well as 4-propyl-5-[2'-(1H-tetrazol-5-yl)biphenyl-4-ylmethyl]oxazole-2-carboxylic acid and 4-ethoxy-5-[2'-(1H-tetrazol-5-yl)biphenyl-4-ylmethyl]oxazole-2-carboxylic acid can be prepared in a similar manner or by techniques that are well known in the art. For example, compounds where $R^3$ is —O—$C_{1-5}$alkyl (e.g., 5-ethoxy-4-[2'-(1H-tetrazol-5-yl)biphenyl-4-ylmethyl]oxazole-2-carboxylic acid), can be made by the methods described in Thalhammer et al. (2009) *Tetrahedron Letters* 50:1045-1047 and Tussetschläger et al. (2006) *Z. Naturforsch* 61b:420-426.

Example 1

(2R,3R)-2-Hydroxy-4-phenyl-3-({5-propyl-4-[2'-(1H-tetrazol-5-yl)-biphenyl-4-ylmethyl]-oxazole-2-carbonyl}amino)butyric Acid

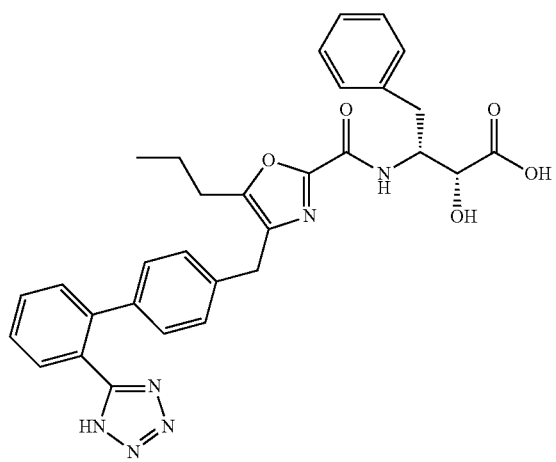 [SMILES: CCCc1oc(C(=O)N[C@H](Cc2ccccc2)[C@@H](O)C(=O)O)nc1Cc1ccc(-c2ccccc2-c2nnn[nH]2)cc1]

A solution of 5-propyl-4-[2'-(1H-tetrazol-5-yl)biphenyl-4-ylmethyl]oxazole-2-carboxylic acid (600 mg, 1 mmol1), (2R,3R)-3-amino-2-hydroxy-4-phenylbutyric acid ethyl ester-.HCl (560 mg, 2.2 mmol), HATU (820 mg, 2.2 mmol), DIPEA (939 μL, 5.4 mmol) and DMF (8 mL) was prepared and stirred overnight. EtOAc (20 mL) and 1M aqueous HCl (10 mL) were added. The organic layer was extracted, dried over $Na_2SO_4$, filtered and concentrated in vacuo to yield the crude intermediate, which was then dissolved in MeOH (5 mL) and 1M aqueous NaOH (5 mL). After 3 hours, the mixture was acidified with AcOH (2 mL) and concentrated in vacuo. Reverse phase HPLC afforded the title compound (30 mg; 92% purity) as well as (2S,3R)-2-hydroxy-4-phenyl-3-({5-propyl-4-[2'-(1h-tetrazol-5-yl)-biphenyl-4-ylmethyl]-oxazole-2-carbonyl}amino)butyric acid (4 mg; 96% purity). For both compounds, MS m/z: [M+H]$^+$ calcd for $C_{31}H_{30}N_6O_5$, 567.23. found 567.6.

Example 2

Following the procedures described in the examples above, and substituting the appropriate starting materials and reagents, compounds IIa-1 to IIa-18 and IIIa-1 to IIIa-18, having the following formula, can also be prepared:

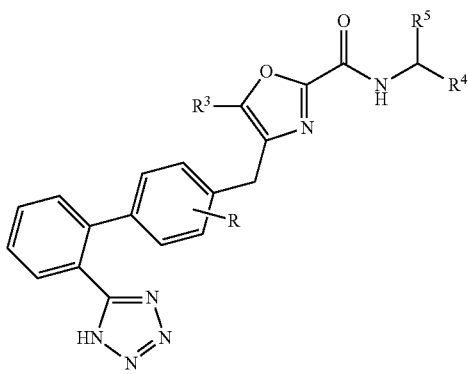

(IIa)

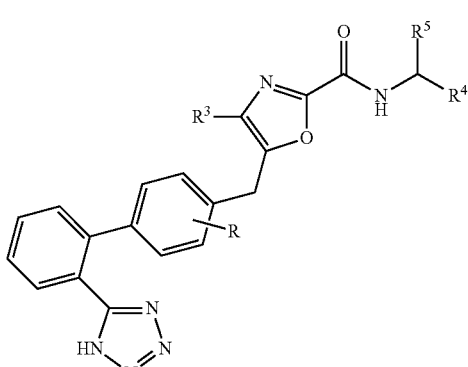

(IIIa)

| # | R | $R^3$ | $R^4$ | $R^5$ |
|---|---|---|---|---|
| 1 | 3-F | ethoxy | —$CH_2SH$ | benzyl |
| 2 | — | propyl | —$CH_2SH$ | i-butyl |
| 3 | 2-F | propyl | —$CH_2COOH$ | 2-Cl-benzyl |
| 4 | — | propyl | —$CH_2COOH$ | 2-Br-benzyl |
| 5 | 2-F | ethoxy | —$CH_2COOH$ | benzyl |
| 6 | 2-F | propyl | —$CH_2COOH$ | 2-F-benzyl |
| 7 | — | ethoxy | —$CH_2COOH$ | 2-$CH_3$-benzyl |
| 8 | — | propyl | —$CH_2COOH$ | 2-$CF_3$-benzyl |
| 9 | 3-F | ethoxy | —CH(OH)COOH | benzyl |
| 10 | — | propyl | —CH(OH)C(O)$OCH_3$ | benzyl |
| 11 | — | propyl | —CH(OH)COOH | 2-Cl-benzyl |
| 12 | 3,5-diF | propyl | —$CH_2$C(O)$OCH_3$ | benzyl |
| 13 | 3,5-diF | ethoxy | —$CH_2$C(O)$OCH_3$ | 2-Cl-benzyl |
| 14 | — | ethoxy | —$CH_2$C(O)$OCH_3$ | 2-$CH_3$-benzyl |
| 15 | — | propyl | —$CH_2$—N(OH)C(O)H | benzyl |
| 16 | 3,5-diF | ethoxy | —$CH_2$C(O)NH(OH) | benzyl |
| 17 | — | propyl | —$CH_2$C(O)NH(OH) | 2-Cl-benzyl |
| 18 | — | propyl | —CH(OH)C(O)NH(OH) | benzyl |

Preparation 5

4-(2'-Acetylsulfamoylbiphenyl-4-ylmethyl)-5-propyloxazole-2-carboxylic acid

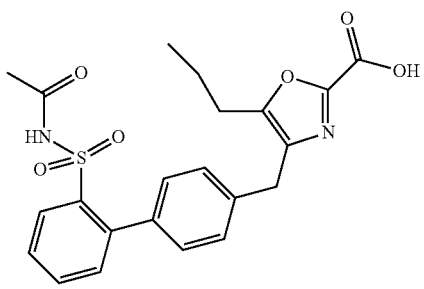 [SMILES: CCCc1oc(C(=O)O)nc1Cc1ccc(-c2ccccc2S(=O)(=O)NC(C)=O)cc1]

The title compound can be prepared in a manner similar to Preparation 4, using a protected sulfonamide, followed by a deprotection step.

Compounds such as 4-(2'-acetylsulfamoylbiphenyl-4-ylmethyl)-5-ethoxyoxazole-2-carboxylic acid, 5-(2'-acetylsulfamoylbiphenyl-4-ylmethyl)-4-propyloxazole-2-carboxylic acid, and 5-(2'-acetylsulfamoylbiphenyl-4-ylmethyl)-4-ethoxyoxazole-2-carboxylic acid can be prepared in a similar manner.

Example 3

Following the procedures described in the examples above, and substituting the appropriate starting materials and reagents, compounds IIb-1 to IIb-18 and IIIb-1 to IIIb-18, having the following formula, can also be prepared:

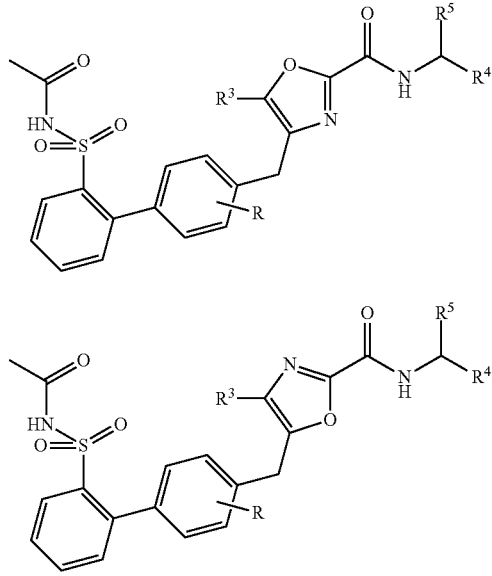

| # | R | $R^3$ | $R^4$ | $R^5$ |
|---|---|---|---|---|
| 1 | 3-F | ethoxy | —CH$_2$SH | benzyl |
| 2 | — | propyl | —CH$_2$SH | i-butyl |
| 3 | 2-F | propyl | —CH$_2$COOH | 2-Cl-benzyl |
| 4 | — | propyl | —CH$_2$COOH | 2-Br-benzyl |
| 5 | 2-F | ethoxy | —CH$_2$COOH | benzyl |
| 6 | 2-F | propyl | —CH$_2$COOH | 2-F-benzyl |
| 7 | — | ethoxy | —CH$_2$COOH | 2-CH$_3$-benzyl |
| 8 | — | propyl | —CH$_2$COOH | 2-CF$_3$-benzyl |
| 9 | 3-F | ethoxy | —CH(OH)COOH | benzyl |
| 10 | — | propyl | —CH(OH)C(O)OCH$_3$ | benzyl |
| 11 | — | propyl | —CH(OH)COOH | 2-Cl-benzyl |
| 12 | 3,5-diF | propyl | —CH$_2$C(O)OCH$_3$ | benzyl |
| 13 | 3,5-diF | ethoxy | —CH$_2$C(O)OCH$_3$ | 2-Cl-benzyl |
| 14 | — | ethoxy | —CH$_2$C(O)OCH$_3$ | 2-CH$_3$-benzyl |
| 15 | — | propyl | —CH$_2$—N(OH)C(O)H | benzyl |
| 16 | 3,5-diF | ethoxy | —CH$_2$C(O)NH(OH) | benzyl |
| 17 | — | propyl | —CH$_2$C(O)NH(OH) | 2-Cl-benzyl |
| 18 | — | propyl | —CH(OH)C(O)NH(OH) | benzyl |

Example 4

Following the procedures described in the examples above, and substituting the appropriate starting materials and reagents, compounds IIc-1 to IIc-21 and IIIc-1 to IIIc-21, having the following formula, can also be prepared:

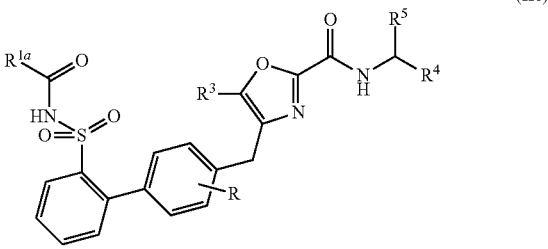

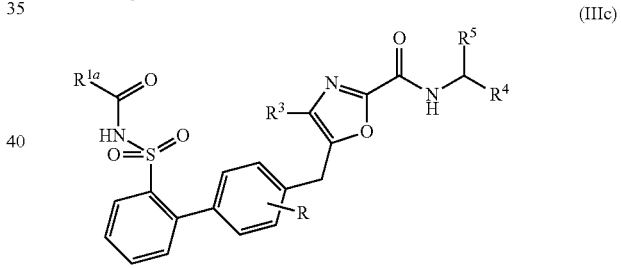

| # | $R^{1a}$ | R | $R^3$ | $R^4$ | $R^5$ |
|---|---|---|---|---|---|
| 1 | —NH(CH$_3$) | 2-F | ethoxy | —CH(OH)COOH | benzyl |
| 2 | —N(CH$_3$)$_2$ | — | propyl | —CH(OH)COOH | benzyl |
| 3 | —NH(CH$_2$CH$_3$) | — | ethoxy | —CH(OH)COOH | benzyl |
| 4 | ethyl | 3-F | propyl | —CH(OH)COOH | benzyl |
| 5 | cyclopropyl | — | ethoxy | —CH(OH)COOH | benzyl |
| 6 | phenyl | — | propyl | —CH(OH)COOH | benzyl |
| 7 | 2F-phenyl | 3,5-diF | ethoxy | —CH(OH)COOH | benzyl |
| 8 | 4-pyridyl | 2-F | propyl | —CH(OH)COOH | benzyl |
| 9 | -3-isoxazolyl-5-methyl | — | ethoxy | —CH(OH)COOH | benzyl |
| 10 | -5-isoxazolyl | — | propyl | —CH(OH)COOH | benzyl |
| 11 | —OCH$_2$CH$_3$ | 3-F | ethoxy | —CH(OH)COOH | benzyl |
| 12 | —CH$_2$OCH$_3$ | — | propyl | —CH(OH)COOH | benzyl |
| 13 | —CH$_2$OCH$_3$ | — | ethoxy | —CH$_2$COOH | 2-Cl-benzyl |
| 14 | —(CH$_2$)$_2$—OCH$_3$ | 3,5-diF | propyl | —CH(OH)COOH | benzyl |
| 15 | 2-pyridyl | 2-F | ethoxy | —CH(OH)COOH | benzyl |
| 16 | —CH$_2$OH | — | propyl | —CH(OH)COOH | benzyl |
| 17 | —CH(CH$_3$)OH | — | ethoxy | —CH(OH)COOH | benzyl |
| 18 | —C(CH$_3$)$_2$OH | 3-F | propyl | —CH(OH)COOH | benzyl |
| 19 | —C(CH$_3$)$_2$NH$_2$ | — | ethoxy | —CH(OH)COOH | benzyl |
| 20 | 1-pyrrolidyl | — | propyl | —CH(OH)COOH | benzyl |
| 21 | 4-morpholinyl | 3,5-diF | ethoxy | —CH(OH)COOH | benzyl |

Preparation 6
5-Propyl-4-{6-[2-(1H-tetrazol-5-yl)phenyl]pyridin-3-ylmethyl}oxazole-2-carboxylic acid

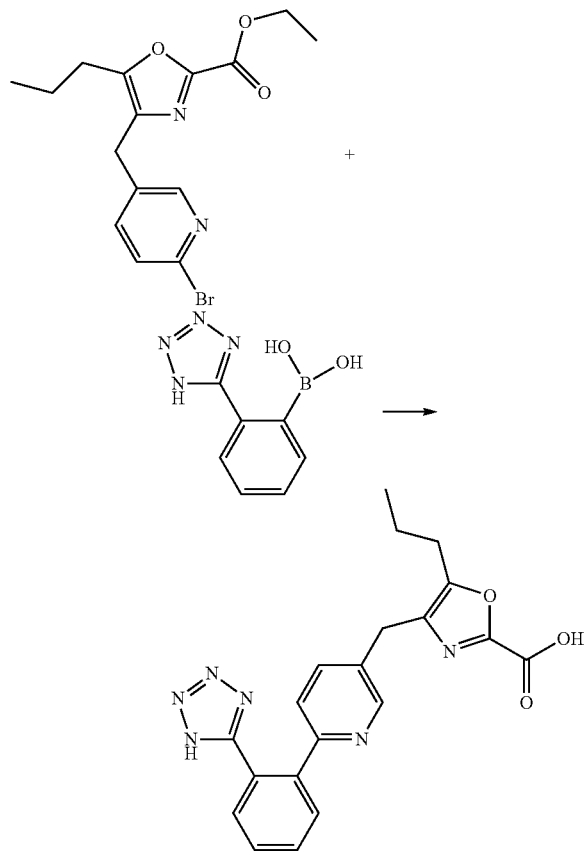

The title compound can be prepared as follows: A solution of (tetrazol-5-yl)phenylboronic acid (1.0 mmol), 4-(6-bromopyridin-3-ylmethyl)-5-propyloxazole-2-carboxylic acid ethyl ester (809 μmol), tetrakis(triphenylphosphine)palladium(0) (40 μmol), 1.0 M NaOH in water (mmol) and MeOH (100 mmol) is sparged shortly, capped under nitrogen and heated in the microwave at 90° C. for 2 hours. The mixture is then filtered to remove the Pd (rinsed with MeOH). The filtrate is then concentrated to remove the McOH, then extracted with EtOAc. The organic layer is extracted with 1N NaOH. The combined aqueous layers are acidified with 1 N HCl to pH 3-4 and extracted with EtOAc. The organics are dried over $MgSO_4$, filtered and concentrated to yield the title compound, which can be used without further purification.

Other compounds, such as 4-propyl-5-{6-[2-(1H-tetrazol-5-yl)phenyl]pyridin-3-ylmethyl}oxazole-2-carboxylic acid, 5-ethoxy-4-{6-[2-(1H-tetrazol-5-yl)phenyl]pyridin-3-ylmethyl}oxazole-2-carboxylic acid, and 4-ethoxy-5-{6-[2-(1H-tetrazol-5-yl)phenyl]pyridin-3-ylmethyl}oxazole-2-carboxylic acid, can be prepared in a similar manner.

Example 5

Following the procedures described in the examples above, and substituting the appropriate starting materials and reagents, compounds IId-1 to IId-22 and IIId-1 to IIId-22, having the following formula, can also be prepared:

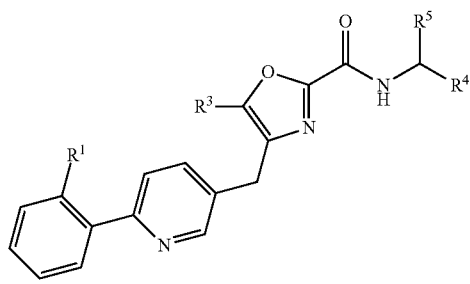
(IId)

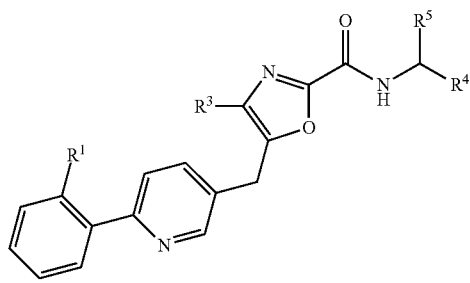
(IIId)

| # | $R^1$ | $R^3$ | $R^4$ | $R^5$ |
|---|---|---|---|---|
| 1 | 1H-tetrazol-5-yl | propyl | —CH$_2$COOH | 2-Cl-benzyl |
| 2 | 1H-tetrazol-5-yl | ethoxy | —CH$_2$COOH | 2-Cl-benzyl |

-continued

| # | R¹ | R³ | R⁴ | R⁵ |
|---|---|---|---|---|
| 3 | 1H-tetrazol-5-yl | propyl | —CH₂COOH | 2-CF₃-benzyl |
| 4 | 1H-tetrazol-5-yl | ethoxy | —CH₂COOH | 2-CF₃-benzyl |
| 5 | 1H-tetrazol-5-yl | propyl | —CH₂COOH | 2-F-benzyl |
| 6 | 1H-tetrazol-5-yl | ethoxy | —CH₂COOH | 2-F-benzyl |
| 7 | 1H-tetrazol-5-yl | propyl | —CH(OH)COOH | benzyl |
| 8 | 1H-tetrazol-5-yl | propyl | —CH₂SH | benzyl |
| 9 | 1H-tetrazol-5-yl | propyl | —CH₂COOH | 2-Br-benzyl |
| 10 | 1H-tetrazol-5-yl | propyl | —CH(OH)COOH | 2-Cl-benzyl |
| 11 | 1H-tetrazol-5-yl | propyl | —CH₂COOH | benzyl |
| 12 | 1H-tetrazol-5-yl | propyl | —CH₂COOH | i-butyl |
| 13 | 1H-tetrazol-5-yl | propyl | —CH(OH)COOH | i-butyl |
| 14 | 1H-tetrazol-5-yl | propyl | —CH(OH)COOH | benzyl |
| 15 | 1H-tetrazol-5-yl | propyl | —CH₂COOH | 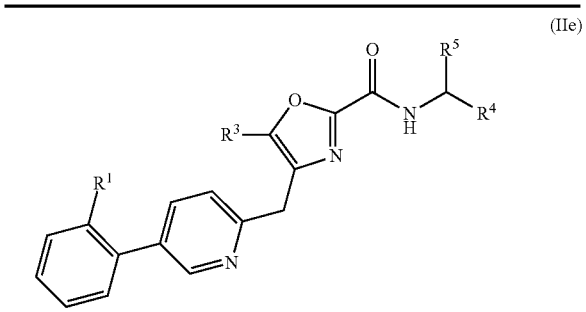 |
| 16 | 1H-tetrazol-5-yl | propyl | —CH₂COOH | 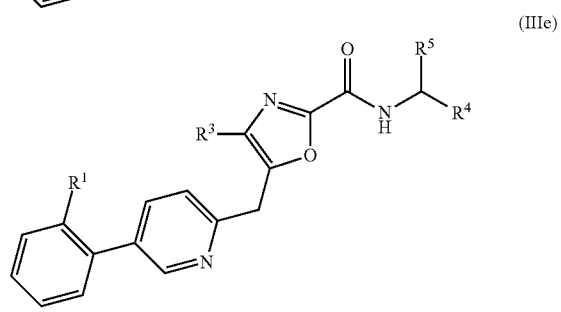 |
| 17 | 1H-tetrazol-5-yl | propyl | —CH₂COOH | 3-F-benzyl |
| 18 | 1H-tetrazol-5-yl | propyl | —CH₂COOH | 4-F-benzyl |
| 19 | —SO₂NH—C(O)CH₃ | propyl | —CH(OH)COOH | benzyl |
| 20 | —SO₂NH—C(O)CH₃ | propyl | —CH₂SH | benzyl |
| 21 | —SO₂NH—C(O)CH₃ | propyl | —CH₂COOH | 2-Cl-benzyl |
| 22 | —SO₂NH—C(O)CH₃ | propyl | —CH₂COOH | benzyl |

Example 6

Following the procedures described in the examples above, and substituting the appropriate starting materials and reagents, compounds IIe-1 to IIe-4 and IIIe-1 to IIIe-4, having the following formula, can also be prepared:

(IIe)

(IIIe)

| # | R¹ | R³ | R⁴ | R⁵ |
|---|---|---|---|---|
| 1 | 1H-tetrazol-5-yl | propyl | —CH(OH)COOH | benzyl |
| 2 | 1H-tetrazol-5-yl | propyl | —CH₂COOH | 2-Cl-benzyl |
| 3 | —SO₂NH—C(O)CH₃ | propyl | —CH(OH)COOH | benzyl |
| 4 | —SO₂NH—C(O)CH₃ | propyl | —CH₂COOH | 2-Cl-benzyl |

Example 7

Following the procedures described in the examples above, and substituting the appropriate starting materials and reagents, compounds IIf-1 to IIf-7 and IIIf-1 to IIIf-7, having the following formula, can also be prepared:

(IIf)

(IIIf)

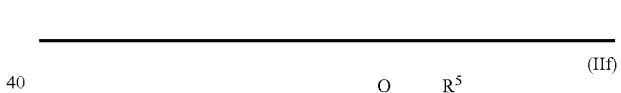

| # | R¹ | R³ | R⁴ | R⁵ |
|---|---|---|---|---|
| 1 | 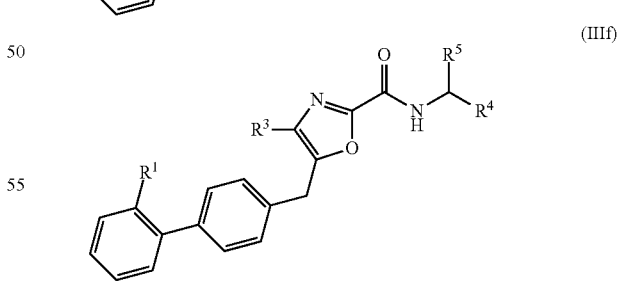 | propyl | —CH₂SH | benzyl |

-continued

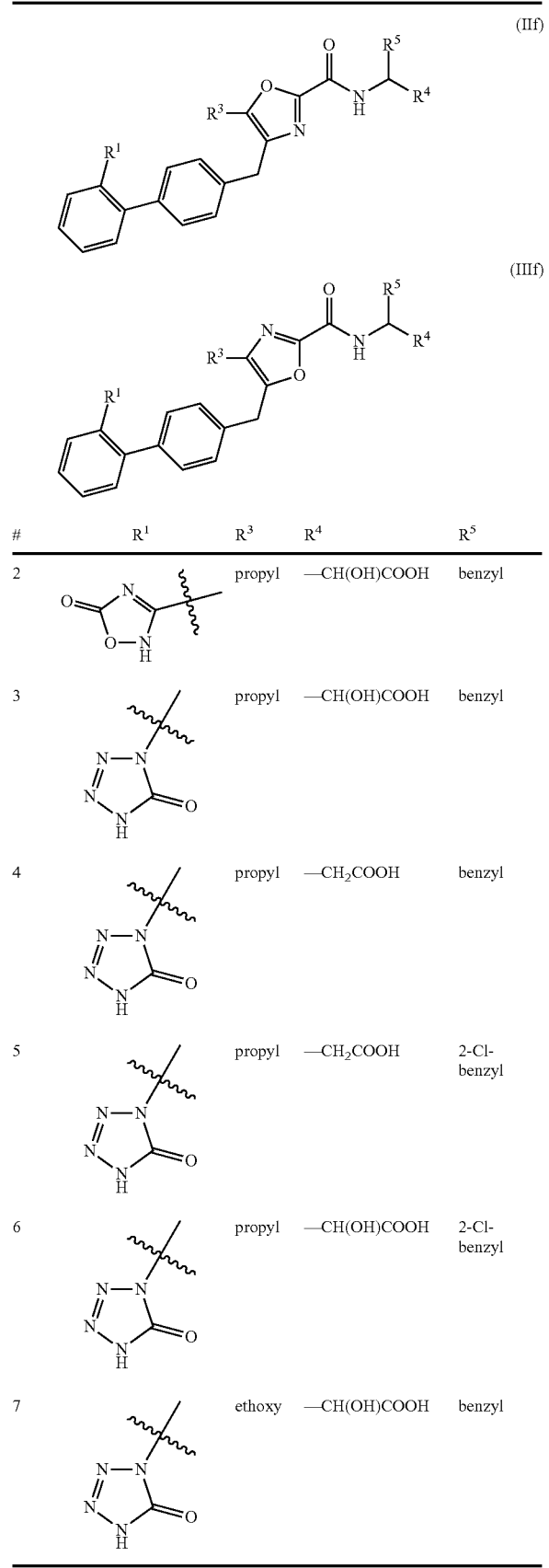

| # | R¹ | R³ | R⁴ | R⁵ |
|---|---|---|---|---|
| 2 | (1,2,4-oxadiazol-5(4H)-one-3-yl) | propyl | —CH(OH)COOH | benzyl |
| 3 | (tetrazolinon-1-yl) | propyl | —CH(OH)COOH | benzyl |
| 4 | (tetrazolinon-1-yl) | propyl | —CH₂COOH | benzyl |
| 5 | (tetrazolinon-1-yl) | propyl | —CH₂COOH | 2-Cl-benzyl |
| 6 | (tetrazolinon-1-yl) | propyl | —CH(OH)COOH | 2-Cl-benzyl |
| 7 | (tetrazolinon-1-yl) | ethoxy | —CH(OH)COOH | benzyl |

Example 8

Following the procedures described in the examples above, and substituting the appropriate starting materials and reagents, compounds IIg-1 to IIg-6 and IIIg-1 to IIIg-6, having the following formula, can also be prepared:

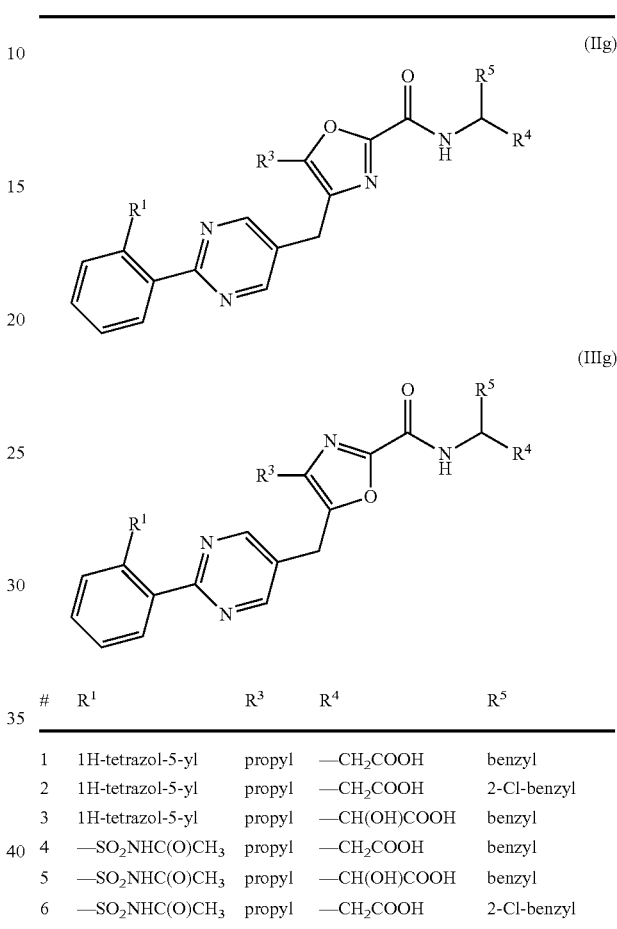

| # | R¹ | R³ | R⁴ | R⁵ |
|---|---|---|---|---|
| 1 | 1H-tetrazol-5-yl | propyl | —CH₂COOH | benzyl |
| 2 | 1H-tetrazol-5-yl | propyl | —CH₂COOH | 2-Cl-benzyl |
| 3 | 1H-tetrazol-5-yl | propyl | —CH(OH)COOH | benzyl |
| 4 | —SO₂NHC(O)CH₃ | propyl | —CH₂COOH | benzyl |
| 5 | —SO₂NHC(O)CH₃ | propyl | —CH(OH)COOH | benzyl |
| 6 | —SO₂NHC(O)CH₃ | propyl | —CH₂COOH | 2-Cl-benzyl |

Example 9

Following the procedures described in the examples above, and substituting the appropriate starting materials and reagents, compounds IIh-1 and IIIh-1, having the following formula, can also be prepared:

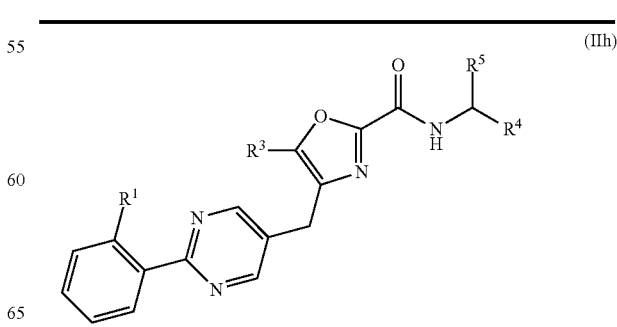

-continued (IIIh)

| # | R$^1$ | R$^3$ | R$^4$ | R$^5$ |
|---|---|---|---|---|
| 1 | 1H-tetrazol-5-yl | propyl | —CH$_2$COOH | 2-Cl-benzyl |
| 1 | 1H-tetrazol-5-yl | propyl | —CH(OH)COOH | benzyl |

Assay 1

AT$_1$ and AT$_2$ Radioligand Binding Assays

These in vitro assays were used to assess the ability of test compounds to bind to the AT$_1$ and the AT$_2$ receptors.

Membrane Preparation from Cells Expressing Human AT$_1$ or AT$_2$ Receptors

Chinese hamster ovary (CHO-K1) derived cell lines stably expressing the cloned human AT$_1$ or AT$_2$ receptors, respectively, were grown in HAM's-F12 medium supplemented with 10% fetal bovine serum, 10 µg/ml penicillin/streptomycin, and 500 µg/ml geneticin in a 5% CO$_2$ humidified incubator at 37° C. AT$_2$ receptor expressing cells were grown in the additional presence of 100 nM PD123,319 (AT$_2$ antagonist). When cultures reached 80-95% confluence, the cells were washed thoroughly in PBS and lifted with 5 mM EDTA. Cells were pelleted by centrifugation and snap frozen in MeOH-dry ice and stored at −80° C. until further use.

For membrane preparation, cell pellets were resuspended in lysis buffer (25 mM Tris/HCl pH 7.5 at 4° C., 1 mM EDTA, and one tablet of Complete Protease Inhibitor Cocktail Tablets with 2 mM EDTA per 50 mL buffer (Roche cat. #1697498, Roche Molecular Biochemicals, Indianapolis, Ind.)) and homogenized using a tight-fitting Dounce glass homogenizer (10 strokes) on ice. The homogenate was centrifuged at 1000×g, the supernatant was collected and centrifuged at 20,000×g. The final pellet was resuspended in membrane buffer (75 mM Tris/HCl pH 7.5, 12.5 mM MgCl$_2$, 0.3 mM EDTA, 1 mM EGTA, 250 mM sucrose at 4° C.) and homogenized by extrusion through a 20G gauge needle. Protein concentration of the membrane suspension was determined by the method described in Bradford (1976) *Anal Biochem.* 72:248-54. Membranes were snap frozen in MeOH-dry ice and stored at −80° C. until further use.

Ligand Binding Assay to Determine Compound Affinities for the Human AT$_1$ and AT$_2$ Angiotensin Receptors Binding assays were performed in 96-well Acrowell filter plates (Pall Inc., cat. #5020) in a total assay volume of 100 µL with 0.2 µg membrane protein for membranes containing the human AT$_1$ receptor, or 2 g membrane protein for membranes containing the human AT$_2$ receptor in assay buffer (50 mM Tris/HCl pH 7.5 at 20° C., 5 mM MgCl$_2$, 25 µM EDTA, 0.025% BSA). Saturation binding studies for determination of K$_d$ values of the ligand were done using N-terminally Europium-labeled angiotensin-II ([Eu]AngII, H—(Eu—N$^1$)-Ahx-Asp-Arg-Val-Tyr-Ile-His-Pro-Phe-OH; PerkinElmer, Boston, Mass.) at 8 different concentrations ranging from 0.1 nM to 30 nM. Displacement assays for determination of pK$_i$ values of test compounds were done with [Eu]AngII at 2 nM and 11 different concentrations of drug ranging from 1 pM to 10 µM. Drugs were dissolved to a concentration of 1 mM in DMSO and from there serially diluted into assay buffer. Nonspecific binding was determined in the presence of 10 µM unlabeled angiotensin-II. Assays were incubated for 120 minutes in the dark, at room temperature or 37° C., and binding reactions were terminated by rapid filtration through the Acrowell filter plates followed by three washes with 200 µL ice cold wash buffer (50 mM Tris/HCl pH 7.5 at 4° C., 5 mM MgCl$_2$) using a Waters filtration manifold. Plates were tapped dry and incubated with 50 µl DELFIA Enhancement Solution (PerkinElmer cat. #4001-0010) at room temperature for 5 minutes on a shaker. Filter-bound [Eu]AngII was quantitated immediately on a Fusion plate reader (PerkinElmer) using Time Resolved Fluorescence (TRF). Binding data were analyzed by nonlinear regression analysis with the GraphPad Prism Software package (GraphPad Software, Inc., San Diego, Calif.) using the 3-parameter model for one-site competition. The BOTTOM (curve minimum) was fixed to the value for nonspecific binding, as determined in the presence of 10 µM angiotensin II. K$_i$ values for drugs were calculated from observed IC$_{50}$ values and the K$_d$ value of [Eu]AngII according to the Cheng-Prusoff equation described in Cheng et al. (1973) *Biochem Pharmacol.* 22(23):3099-108. Selectivities of test compounds for the AT$_1$ receptor over the AT$_2$ receptor were calculated as the ratio of AT$_2$K$_i$/AT$_1$K$_i$. Binding affinities of test compounds were expressed as negative decadic logarithms of the K$_i$ values (pK$_i$).

In this assay, a higher pK$_i$ value indicates that the test compound has a higher binding affinity for the receptor tested. Compounds of the invention tested in this assay are expected to have a pK$_i$ at the AT$_1$ receptor greater than or equal to about 7.0, for example, the compound of Example 1 has a pK$_i$ at the AT$_1$ receptor greater than 7.5.

Assay 2

In Vitro Assays for the Quantitation of Inhibitor Potencies (IC$_{50}$) at Human and Rat NEP, and Human ACE The inhibitory activities of compounds at human and rat NEP and human ACE were determined using in vitro assays as described below.

Extraction of NEP Activity from Rat Kidneys

Rat NEP was prepared from the kidneys of adult Sprague Dawley rats. Whole kidneys were washed in cold PBS and brought up in ice-cold lysis buffer (1% Triton X-114, 150 mM NaCl, 50 mM Tris pH 7.5; Bordier (1981) *J. Biol. Chem.* 256:1604-1607) in a ratio of 5 mL of buffer for every gram of kidney. Samples were homogenized using a polytron hand held tissue grinder on ice. Homogenates were centrifuged at 1000×g in a swinging bucket rotor for 5 minutes at 3° C. The pellet was resuspended in 20 mL of ice cold lysis buffer and incubated on ice for 30 minutes. Samples (15-20 mL) were then layered onto 25 mL of ice-cold cushion buffer (6% w/v sucrose, 50 mM pH 7.5 Tris, 150 mM NaCl, 0.06%, Triton X-114), heated to 37° C. for 3-5 minutes and centrifuged at 1000×g in a swinging bucket rotor at room temperature for 3 minutes. The two upper layers were aspirated off, leaving a viscous oily precipitate containing the enriched membrane fraction. Glycerol was added to a concentration of 50% and samples were stored at −20° C. Protein concentrations were quantitated using a BCA detection system with BSA as a standard.

Enzyme Inhibition Assays

Recombinant human NEP and recombinant human ACE were obtained commercially (R&D Systems, Minneapolis, Minn., catalog numbers 1182-ZN and 929-ZN, respectively). The fluorogenic peptide substrate Mca-BK2 (Mca-Arg-Pro-Pro-Gly-Phe-Ser-Ala-Phe-Lys(Dnp)-OH; Johnson et al. (2000) *Anal. Biochem.* 286: 112-118) was used for the human NEP and ACE assays, and Mca-RRL (Mca-DArg-Arg-Leu-(Dnp)-OH; Medeiros et al. (1997) *Braz. J. Med. Biol. Res.* 30:1157-1162) was used for the rat NEP assay (both from Anaspec, San Jose, Calif.).

The assays were performed in 384-well white opaque plates at room temperature using the respective fluorogenic peptides at a concentration of 10 µM in assay buffer (50 mM Tris/HCl at 25° C., 100 mM NaCl, 0.01% Tween-20, 1 µM Zn, 0.025% BSA). Human NEP and human ACE were used at concentrations that resulted in quantitative proteolysis of 5 µM of Mca-BK2 within 20 minutes at room temperature. The rat NEP enzyme preparation was used at a concentration that yielded quantitative proteolysis of 3 µM of Mca-RRL within 20 minutes at room temperature.

Test compounds were diluted to 12 concentrations from 10 µM to 20 µM in Assay Buffer. Assays were started by adding 25 µL of enzyme to 12.54 of test compound at each of the 12 concentrations. Test compounds were allowed to equilibrate with the enzyme for 10 minutes before 12.5 µL of the fluorogenic substrates were added to initiate the reaction. Reactions were terminated by the addition of 10 µL of 3.6% glacial acetic acid after 20 minutes of incubation.

For sulfhydryl-containing test compounds, the test compounds may be diluted in Assay Buffer containing a 400 µM concentration of tris(2-carboxyethyl)phosphine hydrochloride (Thermo Scientific, Rockford, Ill.) (TCEP). The test compounds are then allowed to reduce for 40 minutes at room temperature before adding the enzyme. Test compounds are then allowed to equilibrate with the enzyme for 20 minutes before adding the fluorogenic substrates. Reactions are terminated as above.

Plates were read on a fluorometer with excitation and emission wavelengths set to 320 nm and 405 nm, respectively. Raw data (relative fluorescence units) were normalized to % activity from the average high readings (no inhibition, 100% enzyme activity) and average low readings (full inhibition, highest inhibitor concentration, 0% enzyme activity) using three standard NEP and ACE inhibitors, respectively. Non-linear regression of the normalized data was performed using a one site competition model (GraphPad Software, Inc., San Diego, Calif.). Data were reported as $pIC_{50}$ values. Compounds of the invention tested in this assay are expected to have a $pIC_{50}$ for the NEP enzyme greater than or equal to about 6.0, the exception being those compounds that are prodrugs. For example, the compound of Example 1 has a $pIC_{50}$ for the NEP enzyme greater than 6.0.

Assay 3

Pharmacodynamic (PD) Assay for ACE, $AT_1$, and NEP Activity in Anesthetized Rats Male, Sprague Dawley, normotensive rats are anesthetized with 120 mg/kg (i.p.) of inactin. Once anesthetized, the jugular vein, carotid artery (PE 50 tubing) and bladder (URI-1 urinary silicone catheter) are cannulated and a tracheotomy is performed (Teflon Needle, size 14 gauge) to faciliate spontaneous respiration. The animals are then allowed a 60 minute stablization period and kept continuously infused with 5 mL/kg/h of saline (0.9%) throughout, to keep them hydrated and ensure urine production. Body temperature is maintained throughout the experiment by use of a heating pad. At the end of the 60 minute stabilization period, the animals are dosed intravenously (i.v.) with two doses of angiotensin (AngI, 1.0 µg/kg, for ACE inhibitor activity; AngII, 0.1 µg/kg, for $AT_1$ receptor antagonist activity) at 15 minutes apart. At 15 minutes post-second dose of angiotensin (AngI or AngII), the animals are treated with vehicle or test compound. Five minutes later, the animals are additionally treated with a bolus i.v. injection of atrial natriuretic peptide (ANP; 30 µg/kg). Urine collection (into pre-weighted eppendorf tubes) is started immediately after the ANP treatment and continued for 60 minutes. At 30 and 60 minutes into urine collection, the animals are re-challenged with angiotensin (AngI or AngII). Blood pressure measurements are done using the Notocord system (Kalamazoo, Mich.). Urine samples are frozen at −20° C. until used for the cGMP assay. Urine cGMP concentrations are determined by Enzyme Immuno Assay using a commercial kit (Assay Designs, Ann Arbor, Mich., Cat. No. 901-013). Urine volume is determined gravimetrically. Urinary cGMP output is calculated as the product of urine output and urine cGMP concentration. ACE inhibition or $AT_1$ antagonism is assessed by quantifying the % inhibition of pressor response to AngI or AngII, respectively. NEP inhibition is assessed by quantifying the potentiation of ANP-induced elevation in urinary cGMP output.

Assay 4

In Vivo Evaluation of Antihypertensive Effects in the Conscious SHR Model of Hypertension Spontaneously hypertensive rats (SHR, 14-20 weeks of age) are allowed a minimum of 48 hours acclimation upon arrival at the testing site. Seven days prior to testing, the animals are either placed on a restricted low-salt diet with food containing 0.1% of sodium for sodium depleted SHRs (SD-SHR) or are placed on a normal diet for sodium repleted SHRs (SR-SHR). Two days prior to testing, the animals are surgically implemented with catheters into a carotid artery and the jugular vein (PE50 polyethylene tubing) connected via a PE10 polyethylene tubing to a selected silicone tubing (size 0.020 ID×0.037 OD×0.008 wall) for blood pressure measurement and test compound delivery, respectively. The animals are allowed to recover with appropriate post operative care. On the day of the experiment, the animals are placed in their cages and the catheters are connected via a swivel to a calibrated pressure transducer. After 1 hour of acclimation, a baseline measurement is taken over a period of at least five minutes. The animals are then dosed i.v. with vehicle or test compound in ascending cumulative doses every 60 minutes followed by a 0.3 mL saline to clear the catheter after each dose. Data is recorded continuously for the duration of the study using Notocord software (Kalamazoo, Mich.) and stored as electronic digital signals. In some studies, the effects of a single intravenous or oral (gavage) dose are monitored for at least 6 hours after dosing. Parameters measured are blood pressure (systolic, diastolic and mean arterial pressure) and heart rate.

Assay 5

In Vivo Evaluation of Antihypertensive Effects in the Conscious DOCA-Salt Rat Model of Hypertension CD rats (male, adult, 200-300 grams, Charles River Laboratory, USA) are allowed a minimum of 48 hours acclimation upon arrival at the testing site before they are placed on a high salt diet. One week after the start of the high salt diet, a DOCA-salt pellet (100 mg, 21 days release time, Innovative Research of America, Sarasota, Fla.) is implanted subcutaneously and unilateral nephrectomy is performed. On 16 or 17 days post DOCA-salt pellet implantation, animals are implanted surgically with catheters into a carotid artery and the jugular vein with a PE50 polyethylene tubing, which in turn was connected via a PE10 polyethylene tubing to a selected silicone tubing (size 0.020 ID×0.037 OD×0.008 wall) for blood pressure measurement and test compound delivery, respectively. The animals are allowed to recover with appropriate post operative care.

On the day of the experiment, each animal is kept in its cage and connected via a swivel to a calibrated pressure transducer. After 1 hour of acclimation, a baseline measurement is taken over a period of at least five minutes. The animals are then dosed i.v. with a vehicle or test compound in escalating cumulative doses every 60 minutes followed by 0.3 mL of saline to flush the catheter after each dose. In some studies, the effects of a single intravenous or oral (gavage) dose is tested and monitored for at least 6 hours after dosing. Data is recorded continuously for the duration of the study using Notocord software (Kalamazoo, Mich.) and stored as electronic digital signals. Parameters measured are blood pressure (systolic, diastolic and mean arterial pressure) and heart rate. For cumulative and single dosing, the percentage change in mean arterial pressure (MAP, mmHg) or heart rate (HR, bpm) is determined as described for Assay 4.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A compound of formula I:

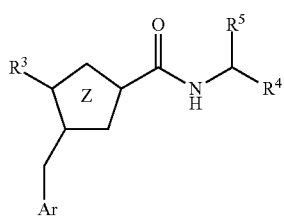

(I)

where: Z is:

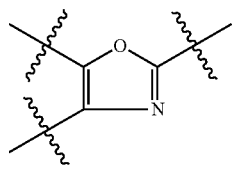 [SMILES: *c1nc(*)c(*)o1]

where the amide portion of the compound of formula I is on the carbon atom between the oxygen ring atom and the nitrogen ring atom and the $R^3$ moiety is on the carbon ring atom adjacent to the oxygen ring atom;

Ar is selected from:

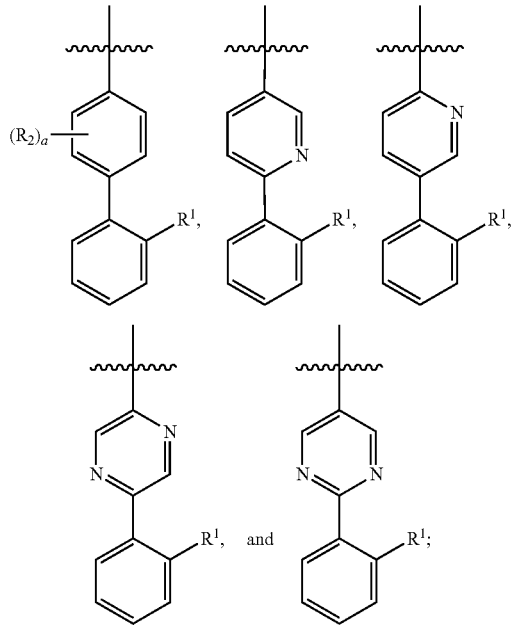

$R^1$ is selected from —COOR, —SO$_2$NHC(O)R$^{1a}$, tetrazolyl,

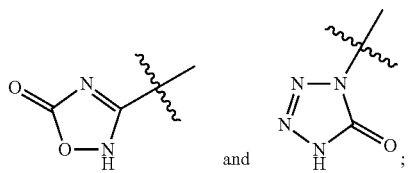

where $R^{1a}$ is —C$_{1-6}$alkyl, —C$_{0-6}$alkylene-OR, —C$_{3-7}$cycloalkyl, —C$_{0-5}$alkylene-NRR, pyridyl, isoxazolyl, methylisoxazolyl, pyrrolidinyl, morpholinyl, and phenyl optionally substituted with halo; where each R is independently selected from H and —C$_{1-6}$alkyl;

a is 0, 1, or 2; $R^2$ is F;

$R^3$ is selected from —C$_{2-5}$alkyl and —O—C$_{1-5}$alkyl;

$R^4$ is —CH(R$^{4b}$)COOR$^{4c}$; where R$^{4b}$ is H or —OH; and R$^{4c}$ is H or —C$_{1-6}$alkyl; and $R^5$ is selected from —C$_{1-6}$alkyl, —CH$_2$-furanyl, —CH$_2$-thiophenyl, benzyl, and benzyl substituted with one or more halo, —CH$_3$, or —CF$_3$ groups;

where each ring in Ar is optionally substituted with 1 to 3 substituents independently selected from —OH, —C$_{1-6}$alkyl, —C$_{2-4}$alkenyl, —C$_{2-4}$alkynyl, —CN, halo, —O—C$_{1-6}$alkyl, —S—C$_{1-6}$alkyl, —S(O)—C$_{1-6}$alkyl, —S(O)$_2$—C$_{1-4}$alkyl, -phenyl, —NO$_2$, —NH$_2$, —NH—C$_{1-6}$alkyl and —N(C$_{1-6}$alkyl)$_2$, wherein each alkyl, alkenyl and alkynyl is optionally substituted with 1 to 5 fluoro atoms;

or a pharmaceutically acceptable salt thereof.

2. The compound of claim 1, where Ar is:

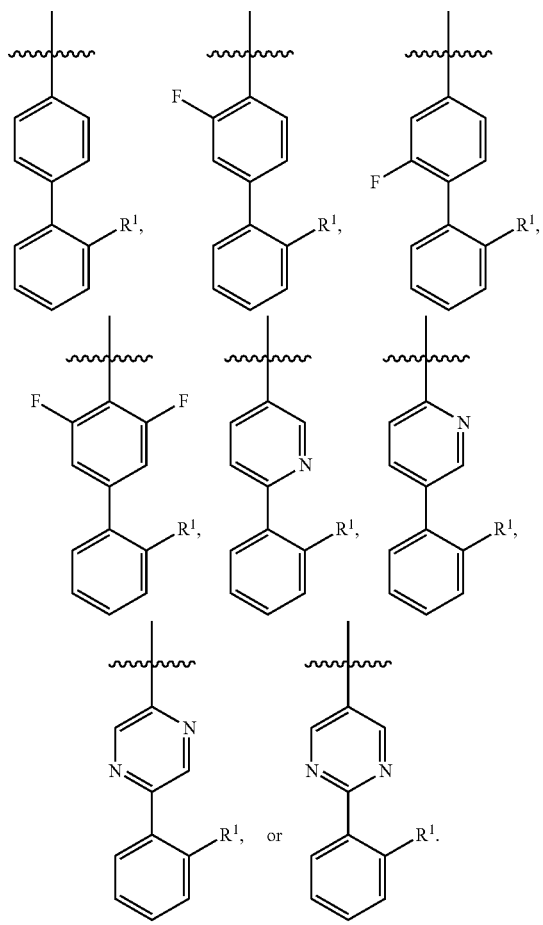

3. The compound of claim 1, where $R^1$ is —SO$_2$NHC(O)CH$_3$, —SO$_2$NHC(O)CH$_2$CH$_3$, —SO$_2$NHC(O)OCH$_3$, —SO$_2$NHC(O)OCH$_2$CH$_3$, —SO$_2$NHC(O)CH$_2$OCH$_3$, —SO$_2$NHC(O)CH$_2$OH, —SO$_2$NHC(O)CH(CH$_3$)OH, —SO$_2$NHC(O)C(CH$_3$)$_2$OH, —SO$_2$NHC(O)CH$_2$OCH$_3$, —SO$_2$NHC(O)(CH$_2$)$_2$OCH$_3$, —SO$_2$NHC(O)-cyclopropyl, —SO$_2$NHC(O)NH(CH$_3$), —SO$_2$NHC(O)N(CH$_3$)$_2$, —SO$_2$NHC(O)NH(CH$_2$CH$_3$), —SO$_2$NHC(O)C(CH$_3$)$_2$NH$_2$, —SO$_2$NHC(O)-2-pyridyl, —SO$_2$NHC(O)-4-pyridyl, —SO$_2$NHC(O)-5-isoxazolyl, —SO$_2$NHC(O)-3-isoxazolyl-5-methyl, —SO$_2$NHC(O)-1-pyrrolidyl, —SO$_2$NHC(O)-4-morpholinyl, —SO$_2$NHC(O)phenyl, —SO$_2$NHC(O)-2-fluorophenyl, 1H-tetrazol-5-yl,

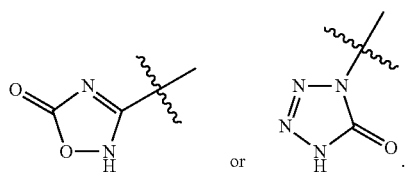 [SMILES: *c1nc(=O)o[nH]1 ; *n1nn[nH]c1=O]

4. The compound of claim 1, where $R^3$ is propyl, ethyl, butyl, or ethoxy.

5. The compound of claim 1, where $R^4$ is —CH(OH)COOH, or —CH$_2$COOH.

6. The compound of claim 1, where $R^4$ is —CH(OH)COOCH$_3$, or —CH$_2$COOCH$_3$.

7. The compound of claim 1, where $R^5$ is i-butyl, —CH$_2$-furan-2-yl, —CH$_2$-thiophen-3-yl, benzyl, 2-bromobenzyl, 2-chlorobenzyl, 2-fluorobenzyl, 3-fluorobenzyl, 4-fluorobenzyl, 2-methylbenzyl, or 2-trifluoromethylbenzyl.

8. A pharmaceutical composition comprising the compound of claim 1 and a pharmaceutically acceptable carrier.

9. The pharmaceutical composition of claim 8 further comprising a second therapeutic agent selected from the group consisting of diuretics, $\beta_1$ adrenergic receptor blockers, calcium channel blockers, angiotensin-converting enzyme inhibitors, AT$_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, vasopressin receptor antagonists, and combinations thereof.

10. The compound of claim 1, wherein $R^1$ is 1H-tetrazol-5-yl.

11. The compound of claim 1, where $R^3$ is —CH$_2$CH$_2$CH$_3$.

12. The compound of claim 1, wherein $R^{4b}$ is —OH.

13. The compound of claim 1, wherein $R^{4c}$ is H.

14. The compound of claim 1, wherein $R^5$ is benzyl.

15. A process for preparing the compound of claim 1, comprising:

(a) coupling a compound of formula 1 with a compound of formula 2:

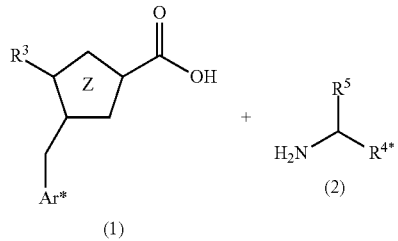

to produce a compound having the formula:

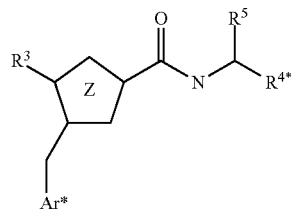

where: Ar* represents Ar—$R^{1*}$, where $R^{1*}$ is $R^1$ or a protected form of $R^1$; and $R^{4*}$ represents $R^4$ or a protected form of $R^4$; and optionally deprotecting the product when $R^{1*}$ is a protected form of $R^1$ and/or $R^{4*}$ is a protected form of $R^4$;

(b) when $R^{1*}$ is a protected form of $R^1$ and/or $R^{4*}$ is a protected form of $R^4$, deprotecting the product of step (a) to produce a compound of formula I.

16. An intermediate useful in the synthesis of the compound of claim 1, selected from the group comprising:

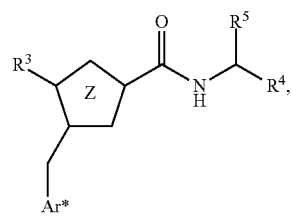

-continued
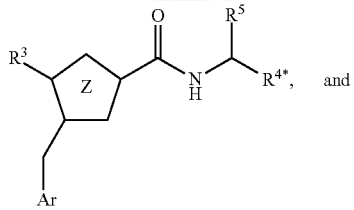
and
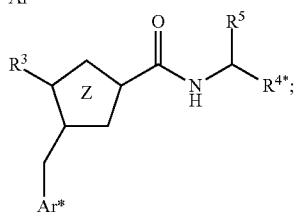
where: Ar* is Ar—R$^{1*}$; R$^{1*}$ is —SO$_2$NH—P$^6$ or tetrazolyl-P$^4$; R$^{4*}$ is —CH(R$^{4b}$)COO—P$^2$; P$^2$ is a carboxy-protecting group; P$^4$ is a tetrazole-protecting group; and P$^6$ is a sulfonamide-protecting group; or a salt thereof; wherein Z, Ar, R$^3$, R$^4$, R$^{4b}$ and R$^5$ are defined as in claim 1.
* * * * *